United States Patent
Roy et al.

(10) Patent No.: US 9,163,047 B2
(45) Date of Patent: *Oct. 20, 2015

(54) SACCHARIDE STRUCTURES AND METHODS OF MAKING AND USING SUCH STRUCTURES

(71) Applicant: MOMENTA PHARMACEUTICALS, INC., Cambridge, MA (US)

(72) Inventors: Sucharita Roy, Tyngsboro, MA (US); Takashi Kei Kishimoto, Lexington, MA (US); Ganesh Kaundinya, Bedford, MA (US)

(73) Assignee: MOMENTA PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,822

(22) Filed: Nov. 8, 2013

(65) Prior Publication Data

US 2014/0200339 A1 Jul. 17, 2014

Related U.S. Application Data

(63) Continuation of application No. 12/595,235, filed as application No. PCT/US2009/045671 on May 29, 2009, now Pat. No. 8,614,314.

(60) Provisional application No. 61/057,354, filed on May 30, 2008.

(51) Int. Cl.
| | | |
|---|---|---|
| A61K 31/70 | (2006.01) | |
| C07H 1/00 | (2006.01) | |
| C07H 5/04 | (2006.01) | |
| C07H 9/04 | (2006.01) | |
| C07H 13/04 | (2006.01) | |
| C07H 15/10 | (2006.01) | |
| C07H 15/18 | (2006.01) | |
| C07H 15/203 | (2006.01) | |
| C07H 23/00 | (2006.01) | |
| C08B 37/00 | (2006.01) | |
| C07H 3/06 | (2006.01) | |

(52) U.S. Cl.
CPC .. *C07H 1/00* (2013.01); *C07H 3/06* (2013.01); *C07H 5/04* (2013.01); *C07H 9/04* (2013.01); *C07H 13/04* (2013.01); *C07H 15/10* (2013.01); *C07H 15/18* (2013.01); *C07H 15/203* (2013.01); *C07H 23/00* (2013.01); *C08B 37/006* (2013.01)

(58) Field of Classification Search
CPC .................................. C07H 3/06; C07H 1/00
See application file for complete search history.

(56) References Cited

U.S. PATENT DOCUMENTS

| | | |
|---|---|---|
| 4,607,025 A | 8/1986 | Petitou et al. |
| 4,761,401 A | 8/1988 | Couchman et al. |
| 4,774,231 A | 9/1988 | Petitou et al. |
| 4,801,583 A | 1/1989 | Petitou et al. |
| 4,804,652 A | 2/1989 | Lormeau et al. |
| 4,818,816 A | 4/1989 | Petitou et al. |
| 4,826,827 A | 5/1989 | Lormeau et al. |
| 4,841,041 A | 6/1989 | van Boeckel et al. |
| 4,943,630 A | 7/1990 | Jacquinet et al. |
| 4,987,223 A | 1/1991 | Choay et al. |
| 4,990,502 A | 2/1991 | Lormeau et al. |
| 5,378,829 A | 1/1995 | Petitou et al. |
| 5,382,570 A | 1/1995 | Petitou et al. |
| 5,529,985 A | 6/1996 | Petitou et al. |
| 5,543,403 A | 8/1996 | Petitou et al. |
| 5,668,274 A | 9/1997 | Petitou et al. |
| RE35,770 E | 4/1998 | Lormeau et al. |
| 5,773,605 A | 6/1998 | Petitou et al. |
| 6,143,730 A * | 11/2000 | Parish et al. ........... 514/54 |
| 6,174,863 B1 | 1/2001 | van Boeckel et al. |
| 6,528,497 B1 | 3/2003 | Basten et al. |
| 6,534,481 B1 | 3/2003 | Driguez et al. |
| 6,573,337 B1 | 6/2003 | Toth et al. |
| 6,670,338 B1 | 12/2003 | Petitou |
| 6,693,173 B2 | 2/2004 | Mamidi et al. |
| 6,693,178 B2 | 2/2004 | Buchwald et al. |
| 7,582,737 B2 | 9/2009 | Hung et al. |
| 7,655,769 B2 | 2/2010 | Hung et al. |
| 8,614,314 B2 | 12/2013 | Sucharita et al. |
| 2004/0010044 A1 | 1/2004 | Clarke et al. |
| 2004/0068108 A1 | 4/2004 | Duchaussoy et al. |
| 2005/0010044 A1 | 1/2005 | Linhardt et al. |
| 2006/0079483 A1 | 4/2006 | Hung et al. |
| 2006/0240473 A1 | 10/2006 | Powell et al. |

(Continued)

FOREIGN PATENT DOCUMENTS

| | | | |
|---|---|---|---|
| EP | 0027089 A1 | 4/1981 | |
| EP | 0037319 A1 | 10/1981 | |
| EP | 0064012 A1 | 11/1982 | |

(Continued)

OTHER PUBLICATIONS

Arungundram, Sailaja et al., "Moldular Synthesis of Heparan Sulfate Oligosaccharides for Structure—Activity Relationship Studies", J. Am.Chem. Soc., 2009, 131 (47), pp. 17394-17405.

(Continued)

*Primary Examiner* — Elli Peselev

(74) *Attorney, Agent, or Firm* — Lando & Anastasi, LLP

(57) ABSTRACT

Described are oligosaccharides having a protecting group at two, a plurality, a majority of, or each position in the oligosaccharide which is amenable to derivatization. Collections, libraries and methods of making and using such oligosaccharides are also described.

5 Claims, 20 Drawing Sheets

(56) References Cited

U.S. PATENT DOCUMENTS

| | | |
|---|---|---|
| 2008/0171722 A1 | 7/2008 | Hung et al. |
| 2009/0137793 A1 | 5/2009 | Hung |

FOREIGN PATENT DOCUMENTS

| | | |
|---|---|---|
| EP | 0064452 A1 | 11/1982 |
| EP | 0082793 A1 | 6/1983 |
| EP | 0084999 A1 | 8/1983 |
| EP | 0113599 A1 | 7/1984 |
| EP | 0165134 A2 | 12/1985 |
| EP | 0287477 A2 | 10/1988 |
| EP | 0300099 A1 | 1/1989 |
| EP | 0301618 A2 | 2/1989 |
| EP | 0454220 A1 | 10/1991 |
| EP | 0529715 A1 | 3/1993 |
| EP | 0589933 A1 | 4/1994 |
| EP | 0904299 A1 | 3/1999 |
| EP | 0912613 A1 | 5/1999 |
| EP | 1032579 A1 | 9/2000 |
| EP | 1049706 A1 | 11/2000 |
| EP | 1049721 A1 | 11/2000 |
| FR | 2440376 A1 | 5/1980 |
| FR | 2461719 A2 | 2/1981 |
| FR | 2478646 A2 | 9/1981 |
| FR | 2614026 A1 | 10/1988 |
| FR | 2749849 A1 | 12/1997 |
| FR | 2751334 A1 | 1/1998 |
| FR | 2773801 A1 | 7/1999 |
| FR | 2773804 A1 | 7/1999 |
| JP | 2000219696 A | 8/2000 |
| JP | 2002522598 A | 7/2002 |
| JP | 2005529910 A | 10/2005 |
| WO | 8101004 A1 | 4/1981 |
| WO | 8102737 A1 | 10/1981 |
| WO | 8203863 A1 | 11/1982 |
| WO | 8401777 A1 | 5/1984 |
| WO | 9222661 A1 | 12/1992 |
| WO | 9222662 A1 | 12/1992 |
| WO | 9747659 A1 | 12/1997 |
| WO | 9803554 A1 | 1/1998 |
| WO | 9925720 A1 | 5/1999 |
| WO | 9936428 A1 | 7/1999 |
| WO | 9936443 A1 | 7/1999 |
| WO | 0009527 A1 | 2/2000 |
| WO | 03093286 A1 | 11/2003 |
| WO | 2004009642 A2 | 1/2004 |

OTHER PUBLICATIONS

Atwell, Graham J., et al., "Monoprotection of .alpha.,.omega.-Alkanediamines with the N-Benzyloxycarbonyl Group" Synthesis, 1984, V. 12, pp. 1032-0133.

International Search Report from International application No. PCT/US2009/45671 mailed Sep. 8, 2009.

Johansson, Rolf, et al., "Regioselective Reductive Ring-opening of 4-Methoxybenzylidene Acetals of Hexopyranosides. Access to a Novel Protecting-group Strategy. Part 1." J. Chem Soc. 1984. V. 10 pp. 2371-2374.

Lohman, Gregory, J. S. et al., "A Stereochemical Surprise at the Late Stage of the Synthesis of Fully N-Differentiated Heparin Oligosaccharides Containing Amino, Acetamido, and N-Sulfonate Groups" J Org Chem. 2004, V 69 pp. 4081-4093. cited byapplicant.

Lohman, Gregory, J. S. et al., "Synthesis of Iduronic Acid Building Blocks for the Modular Assembly of Glycosaminoglycans" J Org Chem. 2003, V 68 pp. 7559-7561.

Orgueira, Hernan, et al., "Modular Synthesis of Heparin Oligosaccharides" Chem. Eur. J., 2003, V 9, No. 1 pp. 140-169.

Prabhu, Arati et al., "New Set of Orthogonal Protecting Groups for the Modular Synthesis of Heparan Sulfate Fragments" 2003 Am. Chem. Soc., Org. Lett., V. 5, No. 26 pp. 4975-4978.

Singh. P.P., et al., "Use of Ferric Chloride in Carbohydrate Chemistry, I. A Quick Method for the Preparation of O-Isopropylidene Derivatives of Carbohydrates" Tetrahedron Letters, No. 5, pp. 439-440, 1977.

Written Opinion from International application No. PCT/US2009145671 mailed Sep. 8, 2009.

Barzu et al., "Preparation and anti-HIV activity of O-acylated heparin and dermatan sulfate derivatives with low anticoagulant effect" Journal of Medicinal Chemistry, 36(23):3546-3555 (1993).

International Preliminary Report on Patentability for Application No. PCT/US2009/45671 issued Nov. 30, 2010.

* cited by examiner

US 9,163,047 B2

SACCHARIDE STRUCTURES AND METHODS OF MAKING AND USING SUCH STRUCTURES

RELATED APPLICATIONS

This application is a continuation of U.S. application Ser. No. 12/595,235 filed May 4, 2011 which is U.S. national stage application under 35 U.S.C. §371 International Application No. PCT/US2009/045671 filed May 29, 2009 which claims priority under 35 U.S.C. §119 from U.S. provisional application Ser. No. 61/057,354 filed May 30, 2008, the entire contents of which is incorporated by reference.

BACKGROUND

Polysaccharides such as heparin, heparan sulfate, chondrotin sulfate, dermatan sulfate and hyaluronic acid are complex and heterogeneous mixtures of saccharide structures. Their biological properties and therapeutic applications are a reflection of this complexity.

SUMMARY

The disclosure is based, in part, on the discovery of saccharide scaffolds that can be used to provide oligosaccharides, e.g., an oligosaccharide having a preselected sequence, as well as substantially homogenous or defined mixtures of oligosaccharides.

Accordingly, in one aspect, the disclosure features an oligosaccharide that is a disaccharide or larger. The oligosaccharide can have a preselected sequence, e.g., a sequence of saccharide structures having a preselected pattern of derivatization. The oligosaccharide allows the design and synthesis of oligosaccharide structures having preselected complex patterns of derivatization, e.g., preselected complex patterns of sulfation or acetylation. In some embodiments, the oligosaccharide has only two different protecting groups. In embodiments the two protecting groups have different reactivities. One protecting group is replaced to a first degree, e.g., substantially completely replaced, with a derivatizing group under selected conditions. The other protecting group gives relatively less, e.g., it gives substantially no derivatization, under the same conditions. The oligosaccharide can be, e.g., a disaccharide, a trisaccharide, a tetrasaccharide, a pentasaccharide, a hexasaccharide, an octasaccharide, a nonasaccharide, a decasaccharide, a dodecasaccharide, tetradecasaccharide, hexadecasaccharide, or octadecasaccharide. (Saccharides of the invention can have an even or odd number of monosaccharide subunits.)

In one embodiment, the disclosure features an oligosaccharide comprising a plurality of disaccharide units, wherein one, two, a plurality, a majority of, or each position amenable to sulfation or acetylation within a disaccharide unit in the plurality is protected either with a first protecting group that allows derivatization, e.g., sulfation or acetylation, or a second protecting group that does not allow derivatization, e.g., sulfation or acetylation, wherein the identity of each protecting group of each disaccharide unit is independent of the identity of any other protecting group in the disaccharide unit, and wherein the identity of each disaccharide unit is independent of the identity of the other disaccharide units within the oligosaccharide.

In one embodiment at least one, two, a plurality, a majority, at least 50, 60, 70, 80, or 90%, or all of the disaccharide units of the plurality, or in the oligosaccharide, have each (or a) position amenable to derivatization protected with one of the two protecting groups. In an embodiment at least one, two, a plurality, a majority, at least 50, 60, 70, 80, or 90%, or all of the disaccharide units of the plurality or in the oligosaccharide have each position amenable to derivatization protected with one of the two protecting groups and in a further embodiment each disaccharide of the plurality or in the oligosaccharide has includes at least one of both protecting groups.

In one embodiment, the disaccharide unit or units within the oligosaccharide are protected with a protecting group that allows derivatization and the protecting group that allows derivatization is the same protecting group at each position. In one embodiment, the disaccharide unit or units are protected with a protecting group that does not allow derivatization and the protecting group that does not allow derivatization is the same protecting group at each position.

In one embodiment, within all of the disaccharide units of the oligosaccharide, each position amenable to derivatization, e.g., sulfation or acetylation, is protected with either a protecting group that allows derivatization, e.g., sulfation or acetylation, or a protecting group that does not allow derivatization, e.g., sulfation or acetylation. In one embodiment, each position protected with a protecting group that allows derivatization is protected with the same protecting group and each position protected with a protecting group that does not allow derivatization is protected with the same protecting group.

In one embodiment, the protecting group can be a hydroxyl protecting group such as, e.g., silyl ethers, ethyl ethers, substituted benzyl ethers and esters. In some embodiments, the protecting group can be an amine protecting group such as, e.g., carbamates and substituted carbamates. In one embodiment, the protecting group that allows derivatization is selected from levulinoyl, benzyl (Bn), benzoyl (Bz), methoxybenzyl (MPM), azide, allyl and silyl ether protecting group (e.g., tBDMS or tBDPS) and the protecting group that does not allow derivatization is selected from levulinoyl, benzyl, benzoyl, MPM, azide, allyl and silyl ether protecting group (e.g., tBDMS or tBDPS), so long as the protecting group that allows derivatization and the protecting group that does not allow derivatization are orthogonal protecting groups. In one embodiment, the protecting group that allows derivatization is a benzoyl and/or a benzoyl containing group and the protecting group that does not allow derivatization is a benzyl, a benzyl containing group and/or an azide. In another embodiment, the protecting group that allows derivatization is a benzyl and/or a benzyl containing group and the protecting group that does not allow derivatization is a benzoyl, a benzoyl containing group and/or an azide. In one embodiment, the protecting group that allows derivatization is a levulinoyl and the protecting group that does not allow derivatization is a benzoyl, a benzoyl containing group and/or an azide. In another embodiment, the protecting group that allows derivatization is a benzoyl and/or a benzoyl containing group and the protecting group that does not allow derivatization is a levulinoyl and/or an azide.

In one embodiment, the disaccharide unit or units are an uronic acid (e.g., iduronic acid and/or glucuronic acid) and a hexosamine (e.g., glucosamine and galactosamine). In one embodiment, the disaccharide unit or units are N-acetylgalactosamine or N-acetylglucosamine and an uronic acid (e.g., glucuronic acid and/or iduronic acid).

In one embodiment, the oligosaccharide comprises a disaccharide having the structure of:

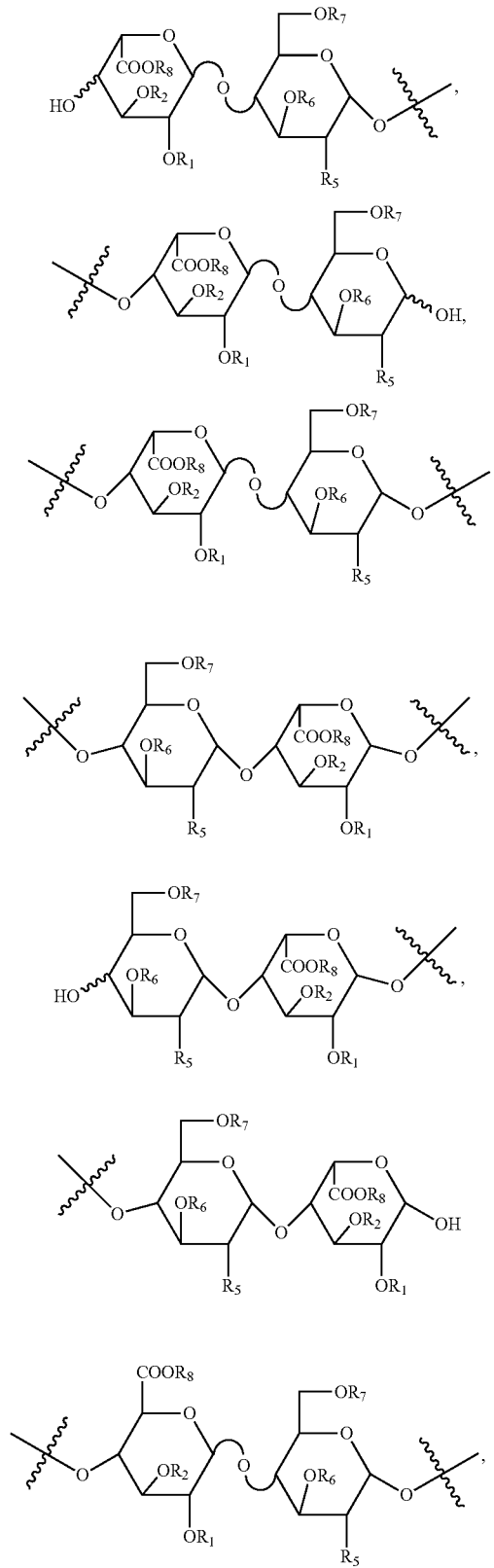

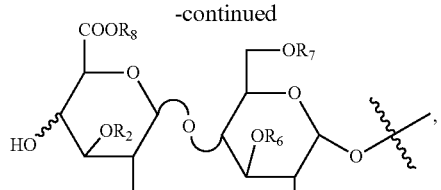

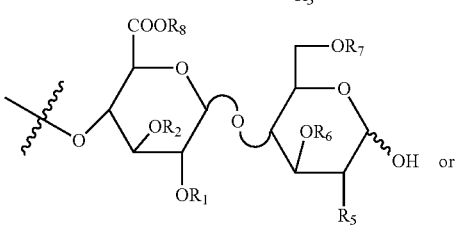

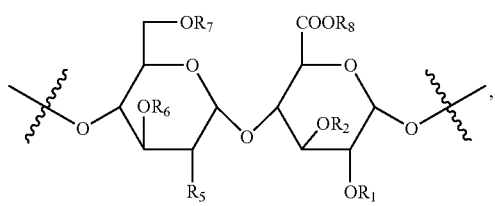

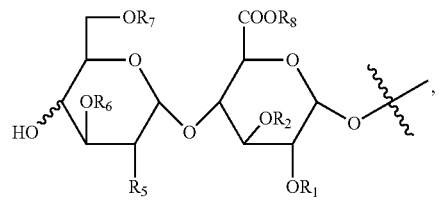

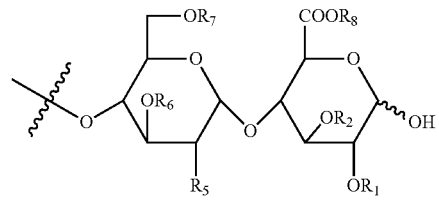

wherein $R_8$ is an alkyl group, e.g., ethyl, methyl, propyl, butyl, pentyl, etc. group, and wherein $R_1$, $R_2$, $R_5$, $R_6$ and $R_7$ are either a first protecting group that allows derivatization, e.g., sulfation or acetylation, or a second protecting group that does not allow derivatization, e.g., sulfation or acetylation. In one embodiment, at each position within the oligosaccharide having the protecting group that allows derivatization, the protecting group is the same protecting group for protecting groups that allow derivatization. In one embodiment, at each position within the oligosaccharide having a protecting group that does not allow derivatization, the protecting group is the same protecting group that does not allow derivatization. In one embodiment, at each position within the oligosaccharide having the protecting group that allows derivatization, the protecting group is the same protecting group and at each position within the oligosaccharide having a protecting group that does not allow derivatization, the protecting group is the same protecting group.

In one embodiment, the oligosaccharide is a decasaccharide that comprises, e.g., consists essentially of:

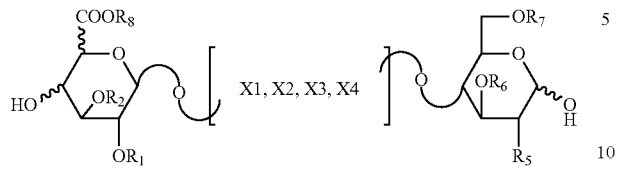

wherein each of X1, X2, X3 and X4 is independently A or B, and wherein
A is and B is

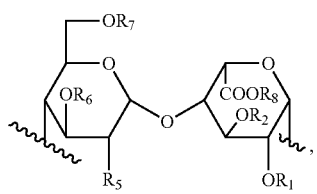

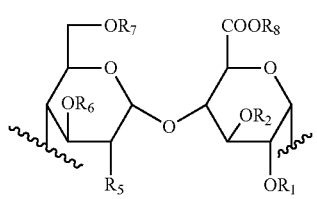

and wherein $R_8$ for each occurrence of A or B is an alkyl group, e.g., an ethyl, methyl, propyl, butyl, pentyl, etc. group and wherein $R_1$, $R_2$, $R_5$, $R_6$, and $R_7$ for each occurrence of A or B is a protecting group selected from either a first protecting group that allows derivatization, e.g., sulfation or acetylation, or a second protecting group that does not allow derivatization, e.g., sulfation or acetylation. In one embodiment, at each position within the oligosaccharide having the protecting group that allows derivatization, the protecting group is the same protecting group. In one embodiment, at each position within the decasaccharide having a protecting group that does not allow derivatization, the protecting group is the same protecting group. In one embodiment, at each position within the decasaccharide having the protecting group that allows derivatization, the protecting group is the same protecting group and at each position within the decasaccharide having a protecting group that does not allow derivatization, the protecting group is the same protecting group. In embodiments, the selection of one or more of $R_1$, $R_2$, $R_5$, $R_6$, and $R_7$ can differ between a first and second group A, an A and B, or a first and second B.

In one embodiment, the oligosaccharide is a decasaccharide that comprises, e.g., consists essentially of:

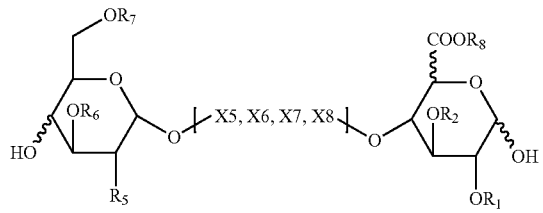

wherein each of X5, X6, X7 and X8 is independently C or D, and wherein
C is: and D is:

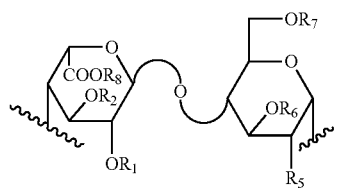

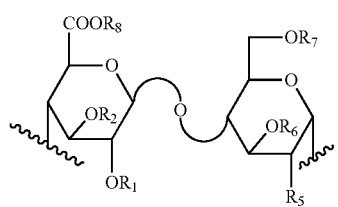

and wherein $R_8$ for each occurrence of C or D is an alkyl group, e.g., an ethyl, methyl, propyl, butyl, pentyl, etc. group and wherein $R_1$, $R_2$, $R_5$, $R_6$, and $R_7$ for each occurrence of C or D is a protecting group selected from either a first protecting group that allows derivatization, e.g., sulfation or acetylation, or a second protecting group that does not allow derivatization, e.g., sulfation or acetylation. In one embodiment, at each position within the oligosaccharide having the protecting group that allows derivatization, the protecting group is the same protecting group. In one embodiment, at each position within the decasaccharide having a protecting group that does not allow derivatization, the protecting group is the same protecting group. In one embodiment, at each position within the decasaccharide having the protecting group that allows derivatization, the protecting group is the same protecting group and at each position within the decasaccharide having a protecting group that does not allow derivatization, the protecting group is the same protecting group. In embodiments, the selection of one or more of $R_1$, $R_2$, $R_5$, $R_6$, and $R_7$ can differ between a first and second group C, a C and D, or a first and second D.

The disclosure also features an oligosaccharide, e.g., an oligosaccharide described above, wherein at any position described above as having a protecting group that allows derivatization, there is a sulfate group, and the remaining positions have a protecting group that does not allow derivatization.

The disclosure also features an oligosaccharide, e.g., an oligosaccharide described above, wherein at any position described above as having a protecting group that does not allow derivatization, there is one or more hydrogen, and the remaining positions have a protecting group that allows derivatization.

In one aspect, the disclosure features a disaccharide having a protecting group at two, a plurality, a majority of, or each position in the disaccharide amenable to derivatization. The protecting group at any given position can be a first protecting group that allows derivatization, e.g., sulfation or acetylation, or a second protecting group that does not allow derivatization, e.g., sulfation or acetylation. As described elsewhere herein, these are useful, for providing oligosaccharides, or libraries thereof, having preselected sequences and/or levels or patterns of derivatization, e.g., sulfation or acetylation.

In one embodiment, the disclosure features a protected disaccharide having a protecting group at each position amenable to sulfation or acetylation within the disaccharide, wherein the protecting group at each position is either a first protecting group that allows derivatization, e.g., sulfation or acetylation, or a second protecting group that does not allow derivatization, e.g., sulfation or acetylation, and, e.g., the identity of each protecting group is independent of the identity of a protecting group at any other position in the saccharide structure.

In one embodiment, the disaccharide has a preselected pattern of protecting groups, e.g., which when derivatized will provide a preselected pattern of derivatization, e.g., sulfation or acetylation.

In an embodiment each position amenable to derivatization is protected with one of the two protecting groups and in an embodiment at least one of each group is present in the disaccharide.

In one embodiment, the protecting group can be a hydroxyl protecting group such as, e.g., silyl ethers, ethyl ethers, substituted benzyl ethers and esters. In some embodiments, the protecting group can be an amine protecting group such as, e.g., carbamates and substituted carbamates. In one embodiment, the protecting group that allows derivatization is selected from levulinoyl, benzyl (Bn), benzoyl (Bz), methoxybenzyl (MPM), azide, allyl and silyl ether protecting group (e.g., tBDMS or tBDPS), and the protecting group that does not allow derivatization is selected from levulinoyl, benzyl, benzoyl, MPM, azide, allyl and silyl ether protecting group (e.g., tBDMS or tBDPS), so long as the protecting group that allows derivatization and the protecting group that does not allow derivatization are orthogonal protecting groups. In one embodiment, the protecting group that allows derivatization is a benzoyl and/or a benzoyl containing group and the protecting group that does not allow derivatization is a benzyl, a benzyl containing group and/or an azide. In another embodiment, the protecting group that allows derivatization is a benzyl and/or a benzyl containing group and the protecting group that does not allow derivatization is a benzoyl, a benzoyl containing group and/or an azide. In one embodiment, the protecting group that allows derivatization is a levulinoyl and the protecting group that does not allow derivatization is a benzoyl, a benzoyl containing group and/or an azide. In another embodiment, the protecting group that allows derivatization is a benzoyl and/or a benzoyl containing group and the protecting group that does not allow derivatization is levulinoyl and/or an azide.

In one embodiment, the disaccharide is an uronic acid (e.g., iduronic acid or glucuronic acid) and a hexosamine (e.g., glucosamine, galactosamine). In one embodiment, the disaccharide is N-acetylgalactosamine or N-acetylglucosamine and an uronic acid (e.g., glucuronic acid and/or iduronic acid).

In one embodiment, at least one position within the disaccharide that can form linkages with another saccharide structure is protected with a protecting group. Examples of protecting groups that can be at positions within the disaccharide that are involved with attaching the disaccharide to another saccharide structure can be any orthogonal hydroxyl protecting groups from, e.g., ethers, substituted ethers, silyl ethers, acetals, esters, etc. Exemplary protecting groups include, but are not limited to, levulinoyl, benzoyl, tert-butyldimethylsilyl (tBDMS), tert-butyldiphenylsilyl (tBDPS), 2-Naphthyl (2-NAP) and 9-Fluorenylmethoxycarbonyl (Fmoc).

In one embodiment, the disaccharide has one of the following structures I, II, III or IV:

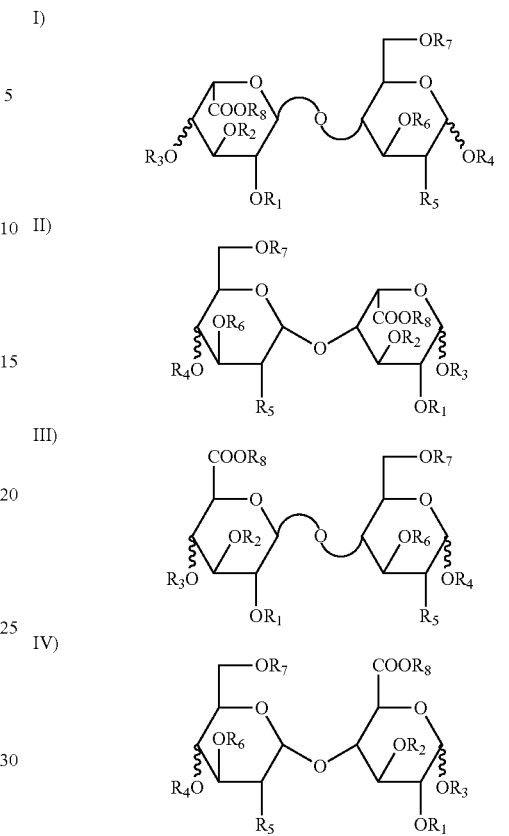

wherein $R_1$, $R_2$, $R_5$, $R_6$ and $R_7$ are protecting groups selected from either a first protecting group that allows derivatization, e.g., sulfation or acetylation, or a second protecting group that does not allow derivatization, wherein the identity of the protecting group at any of $R_1$, $R_2$, $R_5$, $R_6$ and $R_7$ is independent of the identity of a protecting group at any of the other positions; and wherein $R_8$ is a hydrogen or an alkyl group, e.g., an ethyl, methyl, propyl, butyl, pentyl, etc. In one embodiment, the protecting group that allows derivatization is a benzyl, a benzyl containing group and the protecting group that does not allow derivatization is a benzoyl, a benzoyl containing group and/or an azide. In one embodiment, the protecting group that allows derivatization is a benzoyl and/or a benzoyl containing group and the protecting group that does not allow derivatization is a benzyl, a benzyl containing group and/or an azide.

In one embodiment, $R_3$ is a protecting group, e.g., a protecting group described herein, e.g., a levulinoyl, that can be at a position within the monosaccharide that is involved with attaching the monosaccharide to another saccharide structure.

In one embodiment, $R_4$ is a protecting group, e.g., a protecting group described herein, e.g., a benzoyl or a 2Nap, that can be at a position within the monosaccharide that is involved with attaching the monosaccharide to another saccharide structure.

In one embodiment, the disaccharide is any one of the disaccharides described in Table I, Table II, FIG. 6, FIG. 7, FIG. 14 or FIG. 15.

The disaccharides can be incorporated into larger oligosaccharides, e.g., a trisaccharide, a tetrasaccharide, a pentasaccharide, a hexasaccharide, an octasaccharide, a decasaccharide, a dodecasaccharide, tetradecasaccharide, hexadecasaccharide, or octadecasaccharide.

In another aspect, the disclosure features a monosaccharide having a protecting group at two, a plurality of, a majority of, or each position amenable to derivatization within the monosaccharide. The protecting group at any given position can be a first protecting group that allows derivatization, e.g., sulfation or acetylation, or a second protecting group that does not allow derivatization, e.g., sulfation or acetylation. The identity of each protecting group each at position is independent of the protecting group at any other position. As described elsewhere herein, these are useful, for providing disaccharides or larger oligosaccharides, or libraries thereof, having preselected sequences and/or levels or patterns of derivatization, e.g., sulfation or acetylation.

In an embodiment each position amenable to derivatization is protected with one of the two protecting groups and in an embodiment at least one of each group is present.

In one embodiment, the disclosure features a protected monosaccharide having a protecting group at each position within the monosaccharide amenable to sulfation or acetylation, wherein the protecting group at each position is either a first protecting group that allows derivatization, e.g., sulfation or acetylation, or a second protecting group that does not allow derivatization, e.g., sulfation or acetylation, and the identity of a protecting group at each position amendable to derivatization is independent of the identity of a protecting group at any other position amendable to derivatization in the monosaccharide structure.

In one embodiment, the protecting group can be a hydroxyl protecting group such as, e.g., silyl ethers, ethyl ethers, substituted benzyl ethers and esters. In some embodiments, the protecting group can be an amine protecting group such as, e.g., carbamates and substituted carbamates. In one embodiment, the protecting group that allows derivatization is selected from levulinoyl, benzyl (Bn), benzoyl (Bz), methoxybenzyl (MPM), azide, allyl and silyl ether protecting group (e.g., tBDMS or tBDPS), and the protecting group that does not allow derivatization is selected from levulinoyl, benzyl, benzoyl, MPM, azide, allyl and silyl ether protecting group (e.g., tBDMS or tBDPS), so long as the protecting group that allows derivatization and the protecting group that does not allow derivatization are orthogonal protecting groups. In one embodiment, the protecting group that allows derivatization is a benzoyl and/or a benzoyl containing group and the protecting group that does not allow derivatization is a benzyl, a benzyl containing group and/or an azide. In another embodiment, the protecting group that allows derivatization is a benzyl and/or a benzyl containing group and the protecting group that does not allow derivatization is a benzoyl, a benzoyl containing group and/or an azide. In one embodiment, the protecting group that allows derivatization is a levulinoyl and the protecting group that does not allow derivatization is a benzoyl, a benzoyl containing group and/or an azide. In another embodiment, the protecting group that allows derivatization is a benzoyl and/or a benzoyl containing group and the protecting group that does not allow derivatization is levulinoyl and/or an azide.

In one embodiment, the monosaccharide is an uronic acid (e.g., iduronic acid or glucuronic acid) or a hexosamine (e.g., glucosamine, galactosamine). In one embodiment, the monosaccharide is N-acetylgalactosamine, N-acetylglucosamine or an uronic acid (e.g., glucuronic acid and/or iduronic acid).

In one embodiment, at least one position within the monosaccharide that can form linkages with another saccharide structure is protecting with a protecting group. Examples of protecting groups that can be at positions within the monosaccharide that are involved with attaching the monosaccharide to another saccharide structure can be any orthogonal hydroxyl protecting groups from, e.g., ethers, substituted ethers, silyl ethers, acetals, esters, etc. Exemplary protecting groups include, but are not limited to, levulinoyl, benzoyl, tert-butyldimethylsilyl (tBDMS), tert-butyldiphenylsilyl (tBDPS), 2-Naphthalenesulphonyl L-aspartyl-(2-phenethyl)amide (2-NAP) and Fmoc.

In one embodiment, the monosaccharide has one of the following structures:

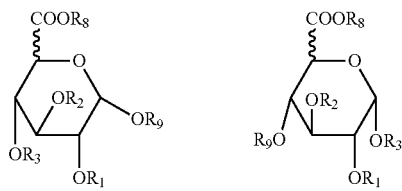

wherein $R_8$ is a hydrogen or an alkyl group, e.g., an ethyl, methyl, propyl, butyl, pentyl, etc.; and wherein $R_1$ and $R_2$ are protecting groups selected from either a first protecting group that allows derivatization, e.g., sulfation or acetylation, or a second protecting group that does not allow derivatization, wherein the identity of the protecting group at $R_1$ and $R_2$ is independent of the protecting group at the other position. In some embodiments, $R_1$ and $R_2$ both have a protecting group that allows derivatization; $R_1$ and $R_2$ both have a protecting group that does not allow derivatization, $R_1$ has a protecting group that allows derivatization and $R_2$ protecting group that does not allow derivatization; or $R_2$ has a protecting group that allows derivatization and $R_1$ has a protecting group that does not allow derivatization. In one embodiment, the protecting group that allows derivatization is a benzyl and the protecting group that does not allow derivatization is a benzoyl. In one embodiment, the protecting group that allows derivatization is a benzoyl and the protecting group that does not allow derivatization is a benzyl.

In one embodiment, $R_9$ is a protecting group, e.g., a protecting group described herein, e.g., a levulinoyl or a tBDMS, that can be at a position within the monosaccharide that can attach the monosaccharide to another saccharide structure.

In one embodiment, the monosaccharide has one of the following structures:

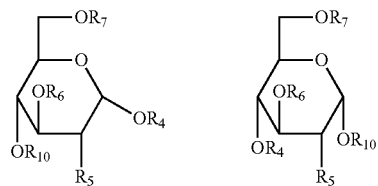

wherein $R_5$, $R_6$ and $R_7$ are protecting groups selected from either a first protecting group that allows derivatization, e.g., sulfation or acetylation, or a second protecting group that does not allow derivatization, wherein the identity of the protecting group at $R_5$, $R_6$ and $R_7$ is independent of the identity of the protecting group at the other positions in the monosaccharide. In some embodiments, $R_5$, $R_6$ and $R_7$ all have a protecting group that allows derivatization; $R_5$, $R_6$ and $R_7$ all have a protecting group that does not allow derivatization, $R_5$ and $R_6$ have a protecting group that allows derivatization and $R_7$ has a protecting group that does not allow derivatization; $R_5$ has a protecting group that allows derivatization and $R_6$ and $R_7$ have a protecting group that does not allow derivatization; $R_5$ and $R_7$ have a protecting group that allows derivatization and $R_6$ has a protecting group that does not allow derivatization; $R_5$ and $R_6$ have a protecting group that does not allow derivatization and $R_7$ has a protecting group that allows derivatization; $R_5$ has a protecting group that does not allow derivatization and $R_6$ and $R_7$ have a protecting group that allows derivatization; $R_5$ and $R_7$ have a protecting group that does not allow derivatization and $R_6$ has a protecting group that allows derivatization. In one embodiment, the protecting group that allows derivatization is a benzyl and/or a benzyl containing group and the protecting group that does not allow derivatization is a benzoyl, a benzoyl containing group and/or an azide. In one embodiment, the protecting group that allows derivatization is a benzoyl and/or a benzyl containing group and the protecting group that does not allow derivatization is a benzyl, a benzyl containing group and/or an azide.

In one embodiment, $R_{10}$ is a protecting group, e.g., a protecting group described herein, e.g., a benzoyl or a 2Nap, that can be at a position within the monosaccharide that is involved with attaching the monosaccharide to another saccharide structure.

In one embodiment, the monosaccharide is a monosaccharide provided in FIG. 1-5, 12 or 13.

In another aspect, the disclosure features a method of making an oligosaccharide that is a disaccharide or larger, e.g., a sequence of saccharide structures having a preselected pattern of derivatization. Embodiments of the method allow the design and synthesis of oligosaccharide structures having preselected complex patterns of derivatization, e.g., preselected complex patterns of sulfation or acetylation. Saccharide structures or subunits, each having the appropriate pattern of protecting groups, are joined together to allow the production of the larger saccharide structure having the preselected pattern of derivatization. A single derivatizing reaction can then provide the preselected pattern of derivatization. Embodiments of the method accomplish this with the use of only two different protecting groups. In an embodiment each of the two protecting groups have different reactivity. One protecting group is replaced to a first degree, e.g., substantially completely replaced, with a derivatizing group under selected conditions. The other protecting group gives relatively less, e.g., it gives substantially no derivatization, under the same conditions. Embodiments rely on a library of different subunits or saccharide structures. The library provides a plurality of oligosaccharide structures having diverse patterns of the two protecting groups. Thus, one can select a first library member having a pattern of protecting groups which, upon derivatization can give a selected pattern of derivatization. As referred to above, the first library member is joined to one or more subsequent library members having selected patterns of protecting groups and selected to provide a pattern of protecting groups. As referred to above, a single reaction can be used to derivatize the entire larger saccharide to provide the oligosaccharide having a preselected pattern of derivatization. The oligosaccharide can be, e.g., a disaccharide, a trisaccharide, a tetrasaccharide, a pentasaccharide, a hexasaccharide, an octasaccharide, a decasaccharide, a dodecasaccharide, tetradecasaccharide, hexadecasaccharide, or octadecasaccharide.

The method includes:

providing a first protected saccharide structure, wherein the saccharide is a monosaccharide or larger, and wherein one, two, a plurality of, a majority of, or all positions in the saccharide structure amenable to derivatization, e.g., sulfation or acetylation, are protected with either a protecting group that allows derivatization, e.g., sulfation or acetylation, or a protecting group that does not allow derivatization, e.g., sulfation or acetylation, and wherein the identity of a protecting group at each position is independent of the identity of a protecting group at any other position in the saccharide structure;

providing a second saccharide structure, wherein the saccharide is a monosaccharide or larger, and optionally, wherein one, two, a plurality of, a majority of, or all positions in the saccharide structure amenable to derivatization, e.g., sulfation or acetylation, are protected with either a protecting group that allows derivatization, e.g., sulfation or acetylation, or a protecting group that does not allow derivatization, e.g., sulfation or acetylation, and wherein the identity of a protecting group at each position is independent of the identity of a protecting group at any other position in the saccharide structure; and attaching the first saccharide structure to the second saccharide structure, to thereby make an oligosaccharide of preselected sequence.

In one embodiment at least one, two, a plurality, a majority, at least 50, 60, 70, 80, or 90%, or all of the protected saccharide units have each (or a) position amenable to derivatization protected with one of the two protecting groups. In an embodiment at least one, two, a plurality, a majority, at least 50, 60, 70, 80, or 90%, or all of the protected saccharide units have each position amenable to derivatization protected with one of the two protecting groups and in a further embodiment each protected saccharide of the includes at least one of both protecting groups.

In one embodiment, the method includes making an oligosaccharide with a sequence having a preselected pattern of derivatization, e.g., a preselected pattern of sulfation or acetylation, e.g., a sequence having a first saccharide structure having a first pattern of derivatization, e.g., a sulfate derivatized at position $R_1$ of an uronic acid, and a second saccharide structure having a second pattern of derivatization, e.g., a sulfate at position $R_6$ of a hexosamine. The method includes:

providing a first protected saccharide structure which when derivatized will provide a saccharide structure having a first preselected pattern of derivatization, wherein the saccharide is a monosaccharide or larger, and wherein all positions in the saccharide structure amenable to derivatization, e.g., sulfation or acetylation, are protected with either a protecting group that allows derivatization, e.g., sulfation or acetylation, or a protecting group that does not allow derivatization, e.g., sulfation or acetylation;

providing a second saccharide structure which when derivatized will provide a saccharide structure having a second preselected pattern of derivatization, wherein the saccharide is a monosaccharide or larger, wherein all positions in the saccharide structure amenable to derivatization, e.g., sulfation or acetylation, are protected with either a protecting group that allows derivatization, e.g., sulfation or acetylation, or a protecting group that does not allow derivatization, e.g., sulfation or acetylation; and attaching the first saccharide structure to the second saccharide structure, to thereby make the oligosaccharide with a sequence having a preselected pattern of derivatization.

In one embodiment, positions in the second saccharide structure that are amenable to derivatization, e.g., sulfation or acetylation, are protected with either a protecting group that allows derivatization, e.g., sulfation or acetylation, or a protecting group that does not allow derivatization, e.g., sulfation or acetylation, and the identity of a protecting group at each position amendable to derivatization is independent of the identity of a protecting group at any other position amendable to derivatization in the saccharide structure.

In one embodiment, if more than one position in the first saccharide structure is protected with a protecting group that allows derivatization, the protecting group that allows derivatization is the same protecting group at each position and/or if more than one position in the first saccharide structure is protected with a protecting group that does not allow derivatization, the protecting group that does not allow derivatization is the same protecting group at each position.

In one embodiment, if more than one position in the second saccharide structure is protected with a protecting group that allows derivatization, the protecting group that allows derivatization is the same protecting group at each position and/or if more than one position in the second saccharide structure is protected with a protecting group that does not allow derivatization, the protecting group that does not allow derivatization is the same protecting group at each position.

In one embodiment, at every position within the oligosaccharide protected with a protecting group that allows derivatization, the protecting group is the same protecting group at each position. In one embodiment, at every position within the oligosaccharide protected with a protecting group that does not allow derivatization, the protecting group is the same protecting group at each position. In one embodiment, at every position within the oligosaccharide protected with a protecting group that allows derivatization, the protecting group is the same protecting group at each position and at every position within the oligosaccharide protected with a protecting group that does not allow derivatization, the protecting group is the same protecting group at each position.

In one embodiment, the protecting group can be a hydroxyl protecting group such as, e.g., silyl ethers, ethyl ethers, substituted benzyl ethers and esters. In some embodiments, the protecting group can be an amine protecting group such as, e.g., carbamates and substituted carbamates. In one embodiment, the protecting group that allows derivatization is selected from levulinoyl, benzyl (Bn), benzoyl (Bz), methoxybenzyl (MPM), azide, allyl and silyl ether protecting group (e.g., tBDMS or tBDPS), and the protecting group that does not allow derivatization is selected from levulinoyl, benzyl, benzoyl, MPM, azide, allyl and silyl ether protecting group (e.g., tBDMS or tBDPS), so long as the protecting group that allows derivatization and the protecting group that does not allow derivatization are orthogonal protecting groups. In one embodiment, the protecting group that allows derivatization is a benzoyl and/or a benzoyl containing group and the protecting group that does not allow derivatization is a benzyl, a benzyl containing group and/or an azide. In another embodiment, the protecting group that allows derivatization is a benzyl and/or a benzyl containing group and the protecting group that does not allow derivatization is a benzoyl, a benzoyl containing group and/or an azide. In one embodiment, the protecting group that allows derivatization is a levulinoyl and the protecting group that does not allow derivatization is a benzoyl, a benzoyl containing group and/or an azide. In another embodiment, the protecting group that allows derivatization is a benzoyl and/or a benzoyl containing group and the protecting group that does not allow derivatization is levulinoyl and/or an azide.

In one embodiment, the method further includes providing a third saccharide structure, wherein the third saccharide structure is a monosaccharide or larger; and attaching the third saccharide structure to the saccharide structure formed from the first and second saccharide structure. In one embodiment, the third saccharide structure has a protecting group at all positions in the saccharide structure amenable to derivatization, e.g., sulfation or acetylation, wherein the protecting group is either a protecting group that allows derivatization, e.g., sulfation or acetylation, or a protecting group that does not allow derivatization, e.g., sulfation or acetylation, and the identity of a protecting group at each position amendable to derivatization is independent of the identity of a protecting group at any other position amendable to derivatization in the first, second or third saccharide structure. In one embodiment, the method can further include providing and attaching a fourth, fifth, sixth, seventh, etc. saccharide structure to make the oligosaccharide. Any of the fourth, fifth, sixth, seventh, etc. saccharide structures can be, e.g., a saccharide structure protected at every position amenable to derivatization, e.g., sulfation or acetylation, with either a protecting group that allows derivatization, e.g., sulfation or acetylation, or a protecting group that does not allow derivatization, e.g., sulfation or acetylation, and the identity of the protecting group at each position amendable to derivatization is independent of the identity of the protecting group at any other position amendable to derivatization in any of the other saccharide structures.

In one embodiment, the saccharide structure (e.g., the first, second, third, fourth, etc. saccharide structure) is a monosaccharide, e.g., a monosaccharide described herein, a disaccharide, e.g., a disaccharide described herein, a tetrasaccharide, a pentasaccharide, a hexasaccharide, an octasaccharide, or a decasaccharide. In one embodiment, the first saccharide structure is a disaccharide, e.g., a disaccharide described herein, and the second saccharide structure is selected from a monosaccharide, a disaccharide, a trisaccharide, a tetrasaccharide, a pentasaccharide, a hexasaccharide, a heptasaccharide, and an octasaccharide.

In one embodiment, the method includes providing a first disaccharide structure, e.g., a disaccharide described herein; attaching a second disaccharide structure, e.g., a disaccharide structure described herein, to the first disaccharide structure to provide a first tetrasaccharide structure; providing a third disaccharide structure, e.g., a disaccharide described herein; attaching a fourth disaccharide structure, e.g., a disaccharide structure described herein, to the third disaccharide structure to provide a second tetrasaccharide structure; attaching the first tetrasaccharide structure to the second tetrasaccharide structure to provide an octasaccharide structure; and attaching a fifth disaccharide structure, e.g., a disaccharide structure described herein, to the octasaccharide structure to thereby provide a decasaccharide structure.

In one embodiment, at least one position within the first saccharide structure that attaches the first saccharide structure to the second saccharide structure is protected with a protecting group. In one embodiment, at least one position within the second saccharide structure that attaches the second saccharide structure to the first saccharide structure is protected with a protecting group. In one embodiment, if a third saccharide structure is attached to the second saccharide structure, the second saccharide structure has a protecting group at a position within the second saccharide structure that attaches to the first saccharide structure and a protecting group at a position within the second saccharide structure that attaches to the third saccharide structure. When the second saccharide structure is attached to a third saccharide structure, the third saccharide structure, preferably, has a protecting group at a position within the third saccharide structure that attaches with the second saccharide structure. In one embodiment, if a fourth saccharide structure is attached to the third saccharide structure, the third saccharide structure has a protecting group at a position within the third saccharide structure that attaches to the second saccharide structure and a protecting group at a position within the third saccharide structure that attaches to the fourth saccharide structure. When the third saccharide structure is attached to a fourth saccharide structure, the fourth saccharide structure, preferably, has a protecting group the position within the fourth saccharide structure that attaches with the third saccharide structure. Preferably every saccharide structure used in the described methods has a protecting group at every position in the saccharide structure that attaches one saccharide structure to another saccharide structure. Examples of protecting groups that can be at positions within the saccharide structures that are involved with attaching one saccharide structure to another can be any orthogonal hydroxyl protecting groups from, e.g., ethers, substituted ethers, silyl ethers, acetals, esters, etc. Exemplary protecting groups include, but are not limited to, levulinoyl, benzoyl, tert-butyldimethylsilyl (tBDMS), tert-butyldiphenylsilyl (tBDPS), 2-Naphthalenesulphonyl L-aspartyl-(2-phenethyl)amide (2-NAP) and Fmoc.

In one embodiment, the first saccharide structure includes an uronic acid (e.g., a glucuronic acid or iduronic acid), a hexosamine (e.g., a glucosamine), or a combination or combinations of an uronic acid (e.g., a glucuronic acid or iduronic acid), and a hexosamine (e.g., a glucosamine). In one embodiment, the oligosaccharide comprises uronic acid (e.g., a glucuronic acid and/or iduronic acid) and hexosamine (e.g., glucosamine) and the positions amendable to derivatization are the positions amendable to sulfation or acetylation in heparin or heparan sulfate. In another embodiment, the first saccharide structure includes an N-acetylgalactosamine, an uronic acid (e.g., a glucuronic acid or iduronic acid), or a combination or combinations of an N-acetylgalactosamine and an uronic acid (e.g., a glucuronic acid or iduronic acid). In one embodiment, the oligosaccharide comprises an N-acetylgalactosamine and an uronic acid (e.g., a glucuronic acid or iduronic acid) and the positions amendable to derivatization are positions amendable to sulfation or acetylation in chondrotin sulfate. In one embodiment, the oligosaccharide comprises an N-acetylgalactosamine and an uronic acid (e.g., a glucuronic acid or iduronic acid) and the positions amendable to derivatization are positions amendable to sulfation or acetylation in dermatan sulfate. In one embodiment, the oligosaccharide comprises an N-acetylglucosamine and an uronic acid (e.g., a glucuronic acid or iduronic acid) and the positions amendable to derivatization are positions amendable to sulfation or acetylation in hyaluronic acid.

In one embodiment, the saccharide structure, e.g., the first, second, third, fourth, etc. saccharide structure is a monosaccharide, a disaccharide or an oligosaccharide larger than a disaccharide as described herein.

In one embodiment, the method further includes deprotecting one or more positions within the saccharide structure or saccharide structures that attaches one saccharide structure to another to form an unprotected moiety or moieties. The deprotected moiety or moieties can then be used to attach one saccharide structure to another. In one embodiment, one saccharide structure, e.g., the first saccharide structure, is attached to another saccharide structure, e.g., the second saccharide structure, using a reaction mixture that comprises a catalyst, e.g., TMSOTf or TESOTf.

In one embodiment, the oligosaccharide being made is an oligosaccharide described herein.

In an embodiment, the method is repeated to form a collection or library of oligosaccharides.

In one embodiment, the method further comprises deprotecting the protecting group that allows derivatization, e.g., sulfation or acetylation, to form an unprotected moiety or moieties. The method can further comprise forming derivative moieties, e.g., sulfate or acetate, at the deprotected position or positions.

In one embodiment, the method includes deprotecting a protecting group that is not amendable to derivatization to form an unprotected moiety or moieties. The method can further include adding hydrogen at the deprotected position or positions not amendable to derivatization.

In an embodiment, the method is repeated to form a collection or library of oligosaccharides having preselected sequences.

In one aspect, the disclosure features a method of making an oligosaccharide structure having a defined level or pattern of derivatization, e.g., sulfation or acetylation, comprising:

providing an oligosaccharide structure, e.g., an oligosaccharide structure having positions in the oligosaccharide structure amenable to derivatization, e.g., sulfation or acetylation, protected with either a protecting group that allows derivatization, e.g., sulfation or acetylation, or a protecting group that does not allow derivatization, e.g., as described herein;

deprotecting a class of protected positions in the oligosaccharide, e.g., deprotecting positions in the oligosaccharide that have protecting groups that allow derivatization, to form unprotected moieties and forming derivatized moieties, e.g., sulfate moieties and acetate moieties, on the deprotected positions.

In one embodiment the method includes:

deprotecting a subsequent second class of protected positions in the oligosaccharide, e.g., deprotecting positions in the oligosaccharide that have protecting groups that do not allow derivatization, to form unprotected moieties and forming hydrogen moieties on the second class of deprotected positions.

In one embodiment the method is repeated to form a library of oligosaccharides having preselected levels of patterns of substituents, e.g., sulfation, acetylation.

Although deprotection is sometimes referred to separately, it is understood that deprotection and derivatization can occur sequentially or simultaneously. In addition, it is understood that forming a derivatized moiety and a hydrogen moiety can occur sequentially or simultaneously.

In one embodiment, the oligosaccharide is an oligosaccharide described herein.

In one aspect, the disclosure features a disaccharide having diverse protecting groups (diversely protected saccharides). The disaccharides can be incorporated into larger structures, e.g., a trisaccharide, a tetrasaccharide, a pentasaccharide, a hexasaccharide, an octasaccharide, a decasaccharide, a dodecasaccharide, tetradecasaccharide, hexadecasaccharide, or octadecasaccharide. These are useful, e.g., for providing oligosaccharides, or libraries thereof, having preselected sequences and/or levels or patterns of derivatization, e.g., sulfation or acetylation.

In one embodiment, the disaccharide has one of the following structures I, II, III or IV:

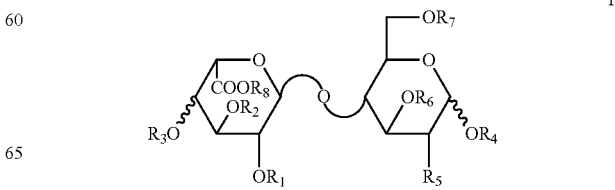

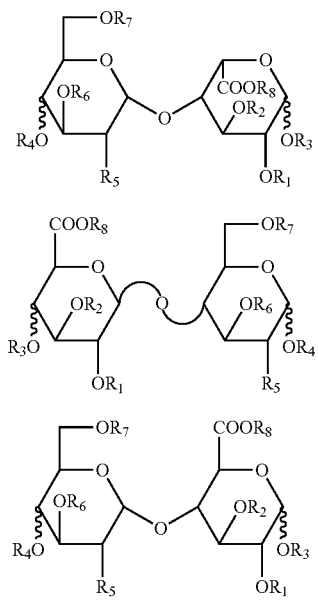

wherein $R_8$ is an alkyl group, e.g., an ethyl, methyl, propyl, butyl, pentyl, etc. group, and wherein each of $R_1$, $R_2$, $R_5$, $R_6$, and $R_7$ are distinct from one another or a subset of $R_1$, $R_2$, $R_5$, $R_6$, and $R_7$ are distinct from one another, e.g., three or more of these positions are distinct from each other. In one embodiment, $R_1$, $R_2$, $R_5$, $R_6$, and $R_7$, are orthogonal protecting groups and thus, each protecting group, $R_1$, $R_2$, $R_5$, $R_6$, and $R_7$, is selected such that any one can be individually removed, without removing the others, to allow reaction of the protected position with another moiety, e.g., to result in the placement of a substituent, e.g., a sulfate or acetate, at the protected moiety. For example, the protecting group at $R_2$ can be removed without removing $R_1$, $R_5$, $R_6$, and $R_7$.

In one embodiment, the protecting group at any of $R_1$, $R_2$, and $R_6$, and $R_7$ can be a hydroxyl protecting group such as, e.g., silyl ethers, ethyl ethers, substituted benzyl ethers and esters. In some embodiments, the protecting group at $R_5$ can be an amine protecting group such as, e.g., carbamates and substituted carbamates. In one embodiment, the protecting group at any of $R_1$, $R_2$, $R_5$, $R_6$, and $R_7$, is selected from levulinoyl, benzyl (Bn), benzoyl (Bz), methoxybenzyl (MPM), azide, allyl and silyl ether protecting group (e.g., tBDMS or tBDPS), as long as two, three, four or more of the protecting groups are orthogonal protecting groups. In one embodiment, $R_1$, $R_2$, $R_5$, $R_6$, and $R_7$ are protecting groups selected from levulinoyl, benzyl, benzoyl, MPM, azide, allyl and silyl ether protecting group (e.g., tBDMS or tBDPS), and none of $R_1$, $R_2$, $R_5$, $R_6$, or $R_7$ are the same protecting group.

In one embodiment, $R_3$ and $R_4$ are protecting groups, e.g., selected from benzoyl and Fmoc, and, e.g., $R_3$ and $R_4$ are not the same protecting group.

In one embodiment, the protecting groups can be: $R_1$ is levulinoyl, $R_2$ is benzyl, $R_3$ is benzoyl, $R_4$ is Fmoc, $R_5$ is azide, $R_6$ is allyl, and $R_7$ is tBDPS; $R_1$ is levulinoyl, $R_2$ is benzyl, $R_3$ is benzoyl, $R_4$ is Fmoc, $R_5$ is NHCBz, $R_6$ is allyl, and $R_7$ is methoxybenzyl; $R_1$ is benzyl, $R_2$ is benzyl, $R_3$ is benzoyl, $R_4$ is Fmoc, $R_5$ is azide, $R_6$ is allyl, and $R_7$ is tBDPS; $R_1$ is benzoyl, $R_2$ is benzyl, $R_3$ is benzoyl, $R_4$ is Fmoc, $R_5$ is NHCBz, $R_6$ is allyl, and $R_7$ is methoxybenzyl; $R_1$ is levulinoyl, $R_2$ is benzyl, $R_3$ is benzoyl, $R_4$ is tBDMS, $R_5$ is azide, $R_6$ is benzyl and $R_7$ is methoxybenzyl; or $R_1$ is benzoyl, $R_2$ is benzyl, $R_3$ is levulinoyl, $R_4$ is tBDMS, $R_5$ is azide, $R_6$ is benzyl, and $R_7$ is methoxybenzyl.

In one embodiment, the disaccharide is a protected disaccharide described herein, e.g., the disaccharide is a disaccharide provided in Table I, Table II, FIG. 6, FIG. 7, FIG. 14 or FIG. 15.

In one aspect, the disclosure features an oligosaccharide made partially or entirely of the diversely protected disaccharides described herein. Moieties protected by a class of protecting group, e.g., $R_1$, can be derivatized, e.g., with a sulfate moiety, or with a hydrogen or hydrogens. The oligosaccharide can be a trisaccharide, a tetrasaccharide, a pentasaccharide, a hexasaccharide, an octasaccharide, a decasaccharide, a dodecasaccharide, tetradecasaccharide, hexadecasaccharide, or octadecasaccharide.

In one embodiment, the oligosaccharide comprises a disaccharide having the structure of:

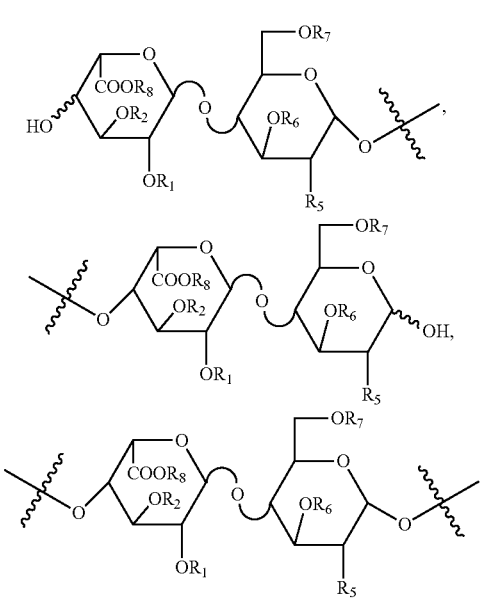

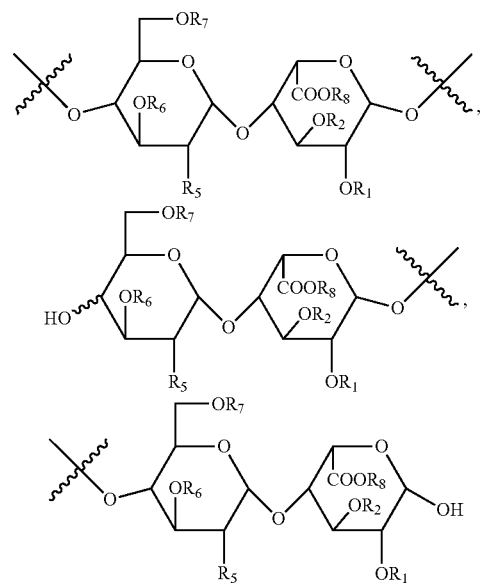

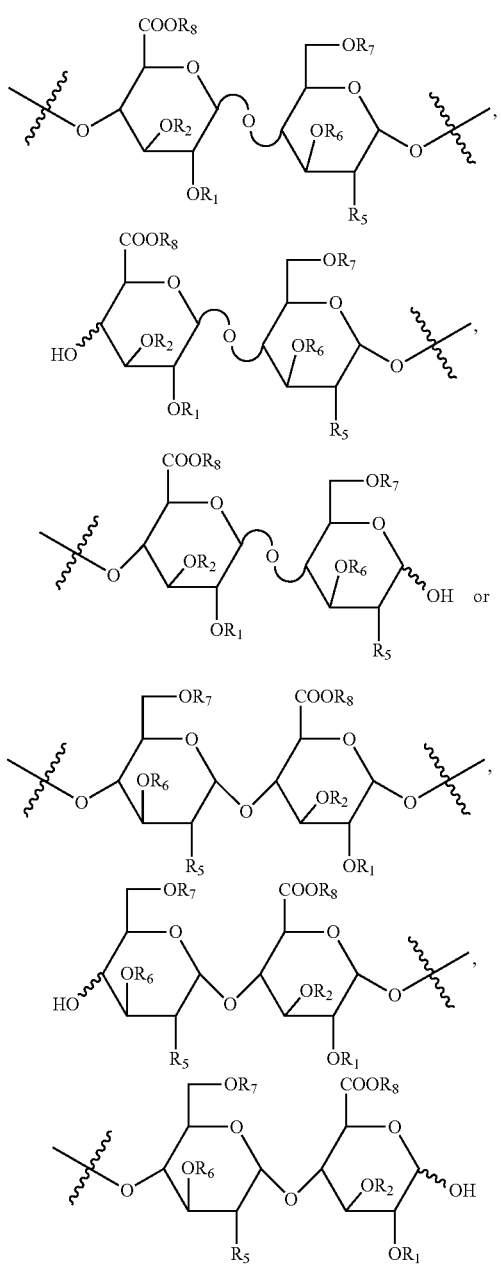

wherein $R_8$ is an alkyl group, e.g., an ethyl, methyl, propyl, butyl, pentyl, etc. group, and wherein each of $R_1$, $R_2$, $R_5$, $R_6$, and $R_7$ are distinct from one another or a subset of $R_1$, $R_2$, $R_5$, $R_6$, and $R_7$ are distinct from one another, e.g., three or more of these positions are distinct from each other. In one embodiment, $R_1$, $R_2$, $R_5$, $R_6$, and $R_7$, are orthogonal protecting groups and thus, each protecting group, $R_1$, $R_2$, $R_5$, $R_6$, and $R_7$, is selected such that any one can be individually removed, without removing the others, to allow reaction of the protected position with another moiety, e.g., to result in the placement of a substituent, e.g., a sulfate, acetate or a hydrogen, at the protected moiety. For example, the protecting group at $R_2$ can be removed without removing $R_1$, $R_5$, $R_6$, and $R_7$.

In one embodiment, the protecting group at any of $R_1$, $R_2$, and $R_6$, and $R_7$ can be a hydroxyl protecting group such as, e.g., silyl ethers, ethyl ethers, substituted benzyl ethers and esters. In some embodiments, the protecting group at $R_5$ can be an amine protecting group such as, e.g., carbamates and substituted carbamates. In one embodiment, the protecting group at any of $R_1$, $R_2$, $R_5$, $R_6$, and $R_7$, is selected from levulinoyl, benzyl (Bn), benzoyl (Bz), methoxybenzyl (MPM), azide, allyl and silyl ether protecting group (e.g., tBDMS or tBDPS), as long as two, three, four or more of the protecting groups are orthogonal protecting groups. In one embodiment, $R_1$, $R_2$, $R_5$, $R_6$, and $R_7$ are protecting groups selected from levulinoyl, benzyl, benzoyl, MPM, azide, allyl and silyl ether protecting group (e.g., tBDMS or tBDPS) and none of $R_1$, $R_2$, $R_5$, $R_6$, or $R_7$ are the same protecting group.

In one embodiment, the protecting groups can be: $R_1$ is levulinoyl, $R_2$ is benzyl, $R_5$ is azide, $R_6$ is allyl, and $R_7$ is tBDPS; $R_1$ is levulinoyl, $R_2$ is benzyl, $R_5$ is NHCBz, $R_6$ is allyl, and $R_7$ is methoxybenzyl; $R_1$ is benzoyl, $R_2$ is benzyl, $R_5$ is azide, $R_6$ is allyl, and $R_7$ is tBDPS; or $R_1$ is benzoyl, $R_2$ is benzyl, $R_5$ is NHCBz, $R_6$ is allyl, and $R_7$ is methoxybenzyl.

In one aspect, the disclosure features a decasaccharide made partially or entirely of the diversely protected disaccharides described herein. These decasaccharides are of interest, in part, because they are of a size which can modulate biological activities.

In one embodiment, the decasaccharide comprises, e.g., consists essentially of:

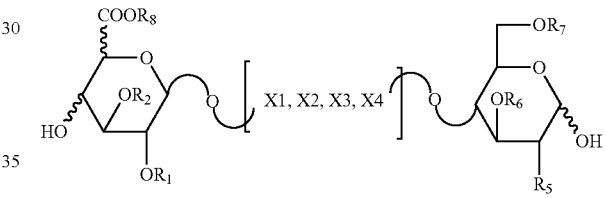

wherein each of X1, X2, X3 and X4 is independently A or B, and wherein
A is and B is

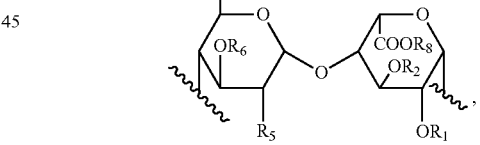

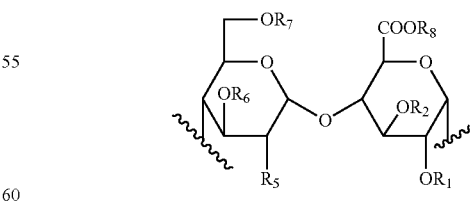

and wherein $R_8$ for each occurrence of A or B is an alkyl group, e.g., an ethyl, methyl, propyl, butyl, pentyl, etc. group and wherein $R_1$, $R_2$, $R_5$, $R_6$, and $R_7$ for each occurrence of A or B each of $R_1$, $R_2$, $R_5$, $R_6$, and $R_7$ are distinct from one another or a subset of $R_1$, $R_2$, $R_5$, $R_6$, and $R_7$ are distinct from one another, e.g., three or more of these positions are distinct from each other. In one embodiment, for each occurrence of A or B none of $R_1$, $R_2$, $R_5$, $R_6$, or $R_7$ within a single A or B is the same as another protecting group within that same A or B. In embodiments the selection of one or more of $R_1$, $R_2$, $R_5$, $R_6$, and $R_7$ can differ between a first and second group A, an A and B, or a first and second B.

In one embodiment, the protecting group at any of $R_1$, $R_2$, and $R_6$, and $R_7$ can be a hydroxyl protecting group such as, e.g., silyl ethers, ethyl ethers, substituted benzyl ethers and esters. In some embodiments, the protecting group at $R_5$ can be an amine protecting group such as, e.g., carbamates and substituted carbamates. In one embodiment, the protecting group at any of $R_1$, $R_2$, $R_5$, $R_6$, and $R_7$, is selected from levulinoyl, benzyl (Bn), benzoyl (Bz), methoxybenzyl (MPM), azide, allyl and silyl ether protecting group (e.g., tBDMS or tBDPS), as long as two, three, four or more of the protecting groups are orthogonal protecting groups. In one embodiment, $R_1$, $R_2$, $R_5$, $R_6$, and $R_7$ are protecting groups selected from levulinoyl, benzyl, benzoyl, MPM, azide, allyl and silyl ether protecting group (e.g., tBDMS or tBDPS), and none of $R_1$, $R_2$, $R_5$, $R_6$, or $R_7$ are the same protecting group.

In one embodiment, the protecting groups can be: $R_1$ is levulinoyl, $R_2$ is benzyl, $R_5$ is azide, $R_6$ is allyl, and $R_7$ is tBDPS; $R_1$ is levulinoyl, $R_2$ is benzyl, $R_5$ is NHCBz, $R_6$ is allyl, and $R_7$ is methoxybenzyl; $R_1$ is benzoyl, $R_2$ is benzyl, $R_5$ is azide, $R_6$ is allyl, and $R_7$ is tBDPS; or $R_1$ is benzoyl, $R_2$ is benzyl, $R_5$ is NHCBz, $R_6$ is allyl, and $R_7$ is methoxybenzyl.

In one embodiment, the decasaccharide comprises, e.g., consisting essentially of:

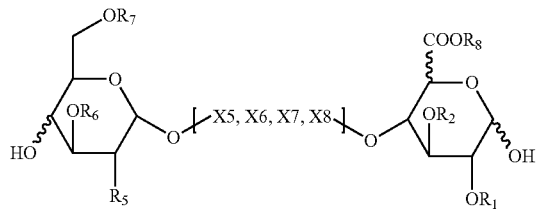

wherein each of X5, X6, X7 and X8 is independently C or D, and wherein
C is: and D is:

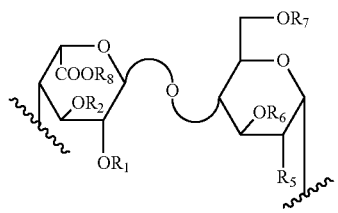

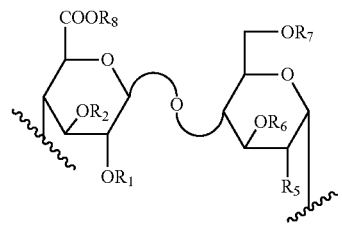

and wherein $R_8$ for each occurrence of C or D is an alkyl group, e.g., an ethyl, methyl, propyl, butyl, pentyl, etc. group and wherein $R_1$, $R_2$, $R_5$, $R_6$, and $R_7$ for each occurrence of C or D each of $R_1$, $R_2$, $R_5$, $R_6$, and $R_7$ are distinct from one another or a subset of $R_1$, $R_2$, $R_5$, $R_6$, and $R_7$ are distinct from one another, e.g., three or more of these positions are distinct from each other. In one embodiment, for each occurrence of C or D none of $R_1$, $R_2$, $R_5$, $R_6$, or $R_7$ within a single C or D is the same as another protecting group within that same C or D. In embodiments the selection of one or more of $R_1$, $R_2$, $R_5$, $R_6$, and $R_7$ can differ between a first and second group C, a C and D, or a first and second D.

In one embodiment, the protecting group at any of $R_1$, $R_2$, and $R_6$, and $R_7$ can be a hydroxyl protecting group such as, e.g., silyl ethers, ethyl ethers, substituted benzyl ethers and esters. In some embodiments, the protecting group at $R_5$ can be an amine protecting group such as, e.g., carbamates and substituted carbamates. In one embodiment, the protecting group at any of $R_1$, $R_2$, $R_5$, $R_6$, and $R_7$, is selected from levulinoyl, benzyl (Bn), benzoyl (Bz), methoxybenzyl (MPM), azide, allyl and tBDPS, as long as two, three, four or more of the protecting groups are orthogonal protecting groups. In one embodiment, $R_1$, $R_2$, $R_5$, $R_6$, and $R_7$ are protecting groups selected from levulinoyl, benzyl, benzoyl, MPM, azide, allyl and tBDPS and none of $R_1$, $R_2$, $R_5$, $R_6$, or $R_7$ are the same protecting group.

In one embodiment, the protecting groups can be: $R_1$ is levulinoyl, $R_2$ is benzyl, $R_5$ is azide, $R_6$ is allyl, and $R_7$ is tBDPS; $R_1$ is levulinoyl, $R_2$ is benzyl, $R_5$ is NHCBz, $R_6$ is allyl, and $R_7$ is methoxybenzyl; $R_1$ is benzoyl, $R_2$ is benzyl, $R_5$ is azide, $R_6$ is allyl, and $R_7$ is tBDPS; or $R_1$ is benzoyl, $R_2$ is benzyl, $R_5$ is NHCBz, $R_6$ is allyl, and $R_7$ is methoxybenzyl.

In one aspect, the disclosure features a tetrasaccharide, e.g., a tetrasaccharide shown in FIG. 16.

In one aspect, the disclosure features a hexasaccharide, e.g., a hexasaccharide shown in FIG. 17.

In one aspect, the disclosure features an oligosaccharide, e.g., a decasaccharide, that includes the following structure:

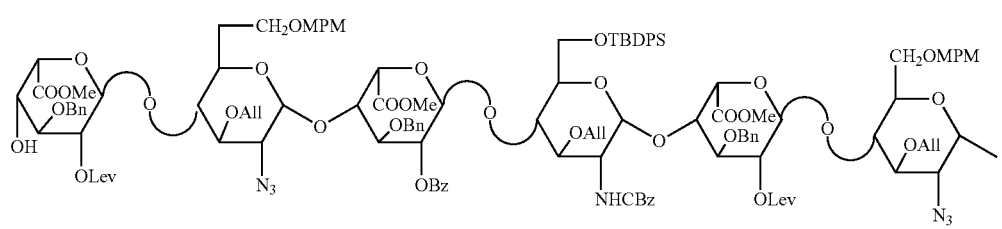

-continued
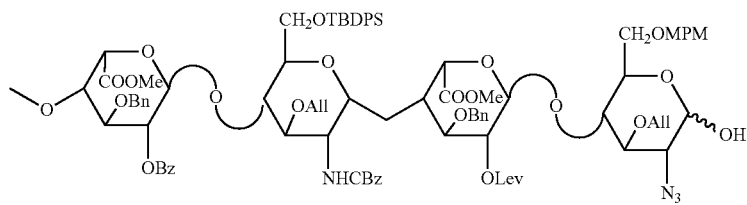
In one aspect, the disclosure features a decasaccharide having the following structure:
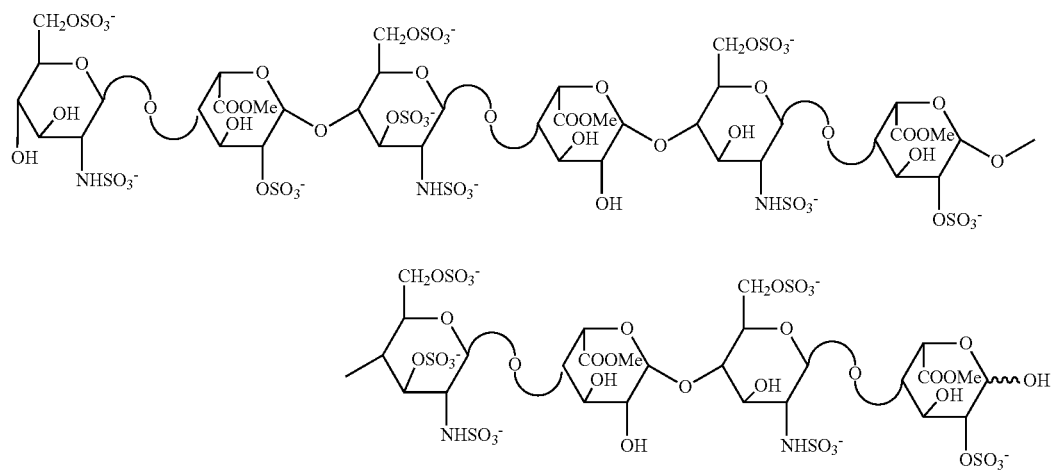
In another aspect, the disclosure features a composition comprising a plurality of decasaccharides, wherein at least 20%, 30%, 40%, 50%, 60%, 70%, 80%, 85%, 90%, 95%, 99% or 100% of the decasaccharides have the following structure:
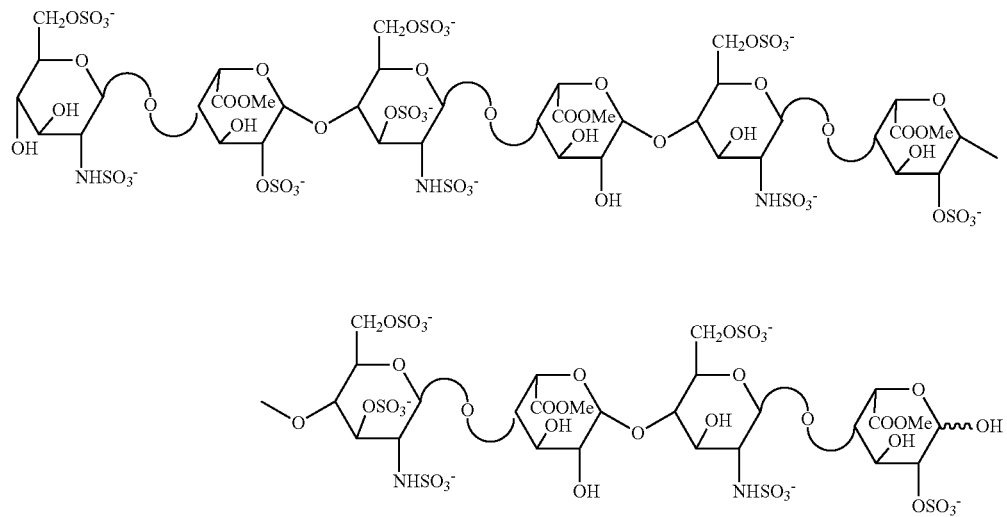

In one embodiment, all of the decasaccharides in the composition have the following structure:

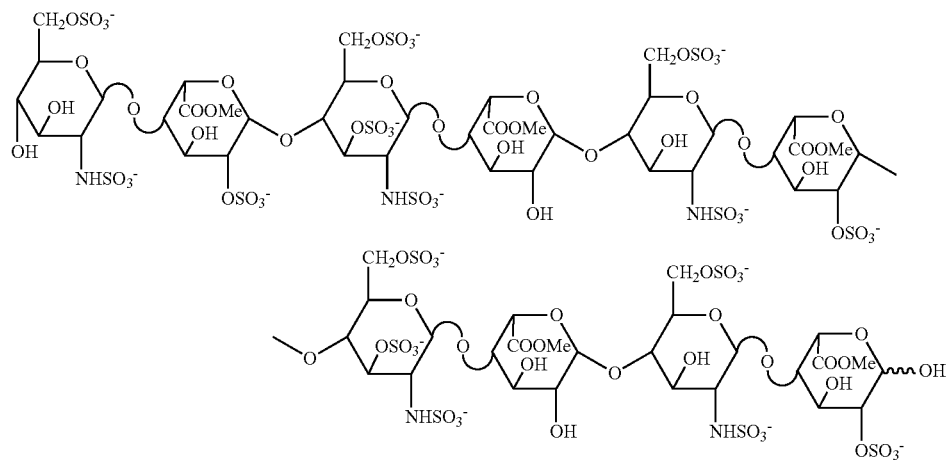

In one aspect, the disclosure features a diversely protected monosaccharide. The monosaccharide can be used to make larger saccharide structures.

In one embodiment, the monosaccharide has the following structure:

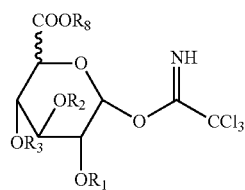

wherein $R_8$ is a hydrogen or an alkyl group, e.g., an ethyl, a methyl, a propyl, a butyl, a pentyl, etc. and wherein $R_1$, $R_2$ group are orthogonal protecting groups. In one embodiment, $R_3$ is a protecting group, e.g., a protecting group selected from benzoyl or Fmoc.

In one embodiment, the protecting group at any of $R_1$ and $R_2$ can be a hydroxyl protecting group such as, e.g., silyl ethers, ethyl ethers, substituted benzyl ethers and esters, so long as the protecting groups at $R_1$ and $R_2$ are orthogonal protecting groups. In one embodiment, the protecting group at any of $R_1$ and $R_2$ is selected from levulinoyl, benzyl (Bn), benzoyl (Bz), methoxybenzyl (MPM), allyl and tBDPS, so long as the protecting groups at $R_1$ and $R_2$ are orthogonal protecting groups.

In one embodiment, the protecting groups at positions $R_1$, $R_2$, and, optionally $R_3$ are different from protecting groups of a glucosamine that has a protecting group at one or more of: attached to an oxygen at position C1 of the glucosamine; attached to position C2 of the glucosamine; attached to an oxygen at position C3 of the glucosamine; and attached to an oxygen at position C6 of the glucosamine.

In one embodiment, the monosaccharide has one of the following structures:

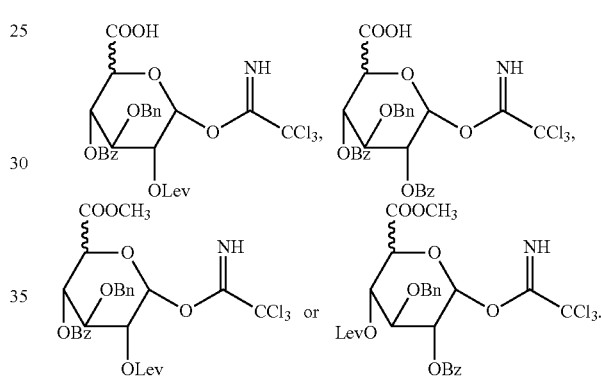

In one embodiment, the monosaccharide has the following structure:

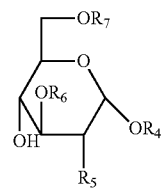

wherein each of $R_5$, $R_6$, and $R_7$ are distinct from one another or a subset of $R_5$, $R_6$, and $R_7$ are distinct from one another, e.g., two or more of these positions are distinct from each other. In one embodiment, $R_5$, $R_6$, and $R_7$ are orthogonal protecting groups and thus, each protecting group, $R_5$, $R_6$, and $R_7$, is selected such that any one can be individually removed, without removing the others, to allow reaction of the protected position with another moiety, e.g., to result in the placement of a substituent, e.g., a sulfate or acetate, at the protected moiety. For example, the protecting group at $R_5$ can be removed without removing $R_6$, and $R_7$.

In one embodiment, the protecting group at any of $R_6$ and $R_7$ can be a hydroxyl protecting group such as, e.g., silyl ethers, ethyl ethers, substituted benzyl ethers and esters. In some embodiments, the protecting group at $R_5$ can be an amine protecting group such as, e.g., carbamates and substituted carbamates. In one embodiment, the protecting group at any of $R_5$, $R_6$, and $R_7$, is selected from levulinoyl, benzyl (Bn), benzoyl (Bz), methoxybenzyl (MPM), azide, allyl and silyl ether protecting group (e.g., tBDMS or tBDPS), as long as two or more of the protecting groups are orthogonal protecting groups. In one embodiment, $R_5$, $R_6$, and $R_7$ are protecting groups selected from levulinoyl, benzyl, benzoyl, MPM, azide, allyl and silyl ether protecting group (e.g., tBDMS or tBDPS), and none of $R_5$, $R_6$, or $R_7$ are the same protecting group.

In one embodiment, $R_4$ is a protecting group, e.g., selected from benzoyl and Fmoc.

In one embodiment, the protecting groups at position $R_5$, $R_6$, $R_7$ and optionally $R_4$ are different from protecting groups of an uronic acid that has a protecting group at one or more of: attached to an oxygen at position C2 of the uronic acid; and attached to an oxygen at position C3 of the uronic acid.

In one embodiment, the monosaccharide has one of the following structures:

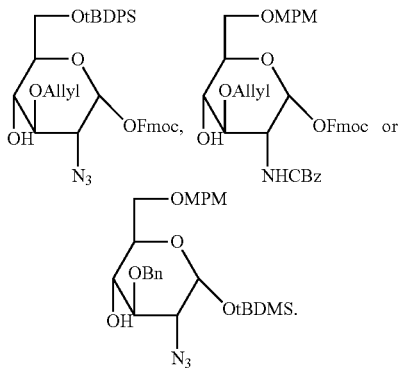

In one embodiment, the monosaccharide is a monosaccharide provided in any of FIGS. 1-5, 12 and 13.

In another aspect, the disclosure features a method of making an oligosaccharide that is a disaccharide or larger, e.g., a sequence of saccharide structures having a preselected pattern of derivatization. Embodiments of the method allow the design and synthesis of oligosaccharide structures having preselected complex patterns of derivatization, e.g., preselected complex patterns of sulfation or acetylation. Saccharide structures or subunits, each having the appropriate pattern of protecting groups, are joined together to allow the production of the larger saccharide structure having the preselected pattern of derivatization. Each saccharide structure can be a diversely protected saccharide structure, e.g., a diversely protected saccharide structure described herein. The library provides a plurality of oligosaccharide structures having diverse patterns of the protecting groups. Thus, one can select a first library member having a pattern of protecting groups which, upon deprotection of a particular protecting group can give a selected pattern of substituents, e.g., sulfate, acetate and hydrogen. As referred to above, the first library member is joined to one or more subsequent library members having selected patterns of protecting groups and selected to provide a pattern of protecting groups. As referred to above, deprotection reactions can be used to removed a particular protecting group within the oligosaccharide and add a substituent at the deprotected position, while maintaining the orthogonal protecting groups at other positions within the oligosaccharide to provide a preselected pattern of substituents, e.g., sulfate, acetate or hydrogen. The oligosaccharide can be, e.g., a disaccharide, a trisaccharide, a tetrasaccharide, a pentasaccharide, a hexasaccharide, an octasaccharide, a decasaccharide, a dodecasaccharide, tetradecasaccharide, hexadecasaccharide, or octadecasaccharide.

The method includes:
providing a first diversely protected saccharide structure, wherein said saccharide structure is a monosaccharide or larger;
providing a second saccharide structure, wherein said second saccharide structure is a monosaccharide or larger, and optionally is a diversely protected saccharide structure; and
attaching said first and second saccharide structures, thereby making an oligosaccharide of preselected sequence.

In one embodiment, the method further includes providing a third saccharide structure, wherein the third saccharide structure is a monosaccharide or larger; and attaching the third saccharide structure to the saccharide structure formed from the first and second saccharide structure. In one embodiment, the third saccharide structure is a diversely protected saccharide structure. In one embodiment, the method can further include providing and attaching a fourth, fifth, sixth, seventh, etc. saccharide structure to make the oligosaccharide. Any of the fourth, fifth, sixth, seventh, etc. saccharide structures can be, e.g., a diversely protected saccharide structure.

In one embodiment, the saccharide structure (e.g., the first, second, third, fourth, etc. saccharide structure) is a monosaccharide, a disaccharide, a tetrasaccharide, a pentasaccharide, a hexasaccharide, an octasaccharide, or a decasaccharide. In one embodiment, the first saccharide structure is a disaccharide and the second saccharide structure is selected from a monosaccharide, a disaccharide, a trisaccharide, a tetrasaccharide, a pentasaccharide, a hexasaccharide, a heptasaccharide, and an octasaccharide.

In one embodiment, the saccharide structure (e.g., the first, second, third, fourth, etc. saccharide structure) is a monosaccharide described herein or a disaccharide a disaccharide described herein.

In one embodiment, the method includes making a disaccharide comprising
providing a first diversely protected monosaccharide described herein and a second diversely protected monosaccharide described herein; and
attaching the first monosaccharide to the second monosaccharide, to thereby make the disaccharide.

In one embodiment, the method includes providing a first disaccharide structure, e.g., a diversely protected disaccharide described herein; attaching a second disaccharide structure, e.g., a diversely protected disaccharide structure described herein, to the first disaccharide structure to provide a first tetrasaccharide structure; providing a third disaccharide structure, e.g., a diversely protected disaccharide described herein; attaching a fourth disaccharide structure, e.g., a diversely protected disaccharide structure described herein, to the third disaccharide structure to provide a second tetrasaccharide structure; attaching the first tetrasaccharide structure to the second tetrasaccharide structure to provide an octasaccharide structure; and attaching a fifth disaccharide structure, e.g., a diversely protected disaccharide structure described herein, to the octasaccharide structure to thereby provide a decasaccharide structure.

In one embodiment, the method further includes deprotecting one or more positions within the saccharide structure or saccharide structures that attaches one saccharide structure to another to form an unprotected moiety or moieties. The deprotected moiety or moieties can then be used to attach one saccharide structure to another. In one embodiment, one saccharide structure, e.g., the first saccharide structure, is attached to another saccharide structure, e.g., the second saccharide structure, using a reaction mixture that comprises a catalyst, e.g., TMSOTf or TESOTf.

In one embodiment, the oligosaccharide is an oligosaccharide described herein.

In an embodiment, the method is repeated to form a collection or library of oligosaccharides.

In one embodiment, the method further comprises deprotecting a protecting group while maintaining orthogonal protecting groups at other positions to form an unprotected moiety or moieties. The method can further comprise forming substituents, e.g., sulfate, acetate, at the deprotected position or positions.

In an embodiment, the method is repeated to form a collection or library of oligosaccharides having preselected sequences.

In one aspect, the disclosure features a method of making an oligosaccharide structure having a defined level or pattern of derivatization, e.g., sulfation, comprising:

providing a diversely protected oligosaccharide structure, e.g., a diversely protected oligosaccharide structure described herein, and optionally of preselected sequence;

deprotecting a class of protected positions in the oligosaccharide, e.g., an oligosaccharide described herein, to form unprotected moieties and forming substituent moieties, e.g., sulfate moieties or acetate moieties, on the deprotected positions.

In one embodiment the method further includes:

deprotecting a subsequent second class of protected positions in the oligosaccharide, e.g., an oligosaccharide described herein, to form a second class of unprotected moieties and forming substituent moieties, e.g., sulfate moieties, acetate moieties or hydrogen moieties, on the second class of deprotected positions.

In one embodiment the method further includes:

deprotecting a subsequent (e.g., a third or fourth) class of protected positions in the oligosaccharide, e.g., an oligosaccharide described herein, to form a subsequent class of unprotected moieties, and forming substituent moieties, e.g., sulfate moieties, acetate moieties, on the subsequent class of deprotected positions.

In an embodiment the method is repeated to form a library of oligosaccharides having preselected levels of patterns of substituents, e.g., sulfation, acetylation.

Although deprotection is sometimes referred to separately, it is understood that deprotection and derivatization can occur sequentially or simultaneously.

In one aspect, the disclosure features method of making a diversely protected monosaccharide, e.g., a diversely protected monosaccharide described herein, comprising:

providing a glucose;

attaching a first protecting group selected from levulinoyl, allyl, benzyl, benzoyl, azide, NHCBz, tBDPS, tBDMS or methoxybenzyl to an oxygen attached to position C3 of the glucose forming a uronic acid from the glucose;

attaching a second protecting group selected from levulinoyl, allyl, benzyl, azide, NHCBz, tBDPS, tBDMS or methoxybenzyl to an oxygen attached to position C2 of the uronic acid, wherein the first protecting group differs from the second protecting group.

In one embodiment, the method includes:

providing a glucose;

attaching a benzyl group at an oxygen attached to position C3 of the glucose;

forming a uronic acid from the glucose; and attaching a levulinoyl or benzoyl to an oxygen attached to position C2 of the uronic acid, to thereby make the monosaccharide.

In one embodiment, the method includes one or more of the steps described in FIG. 1, 3, 5 or 13.

In one aspect, the disclosure features a method of making a monosaccharide, e.g., a diversely protected monosaccharide described herein, comprising:

providing a glucosamine;

attaching a first protecting group selected from levulinoyl, allyl, benzyl, azide, benzoyl, NHCBz, tBDPS, tBDMS or methoxybenzyl at position C2 of the glucosamine;

attaching a second protecting group selected from levulinoyl, allyl, benzyl, azide, benzoyl, NHCBz, tBDPS, tBDMS or methoxybenzyl to an oxygen at position C3 of the glucosamine; and attaching a third protecting group selected from levulinoyl, allyl, benzyl, azide, benzoyl, NHCBz, tBDPS, tBDMS or methoxybenzyl to an oxygen at position C6 of the glucosamine, wherein the first, second and the third protecting groups all differ from each other to thereby make the monosaccharide.

In one embodiment, the method includes:

providing a glucosamine;

attaching an $N_3$ at position C2 of the glucosamine;

attaching an allyl to an oxygen at position C3 of the glucosamine; and attaching a tBDPS, tBDMS or MPM to an oxygen at position C6 of the glucosamine, to thereby make the monosaccharide.

In one embodiment, the method includes one or more of the steps described in FIG. 2, 4 or 12.

In one aspect, the disclosure features a composition that includes a saccharide structure described herein, e.g., a monosaccharide, disaccharide or larger oligosaccharide described herein. In one embodiment, the composition can further include a diluent, excipient or carrier. In one embodiment, the composition is dried or lyophilized.

In one aspect, the disclosure features a compound described any of FIG. 1, 2, 3, 4, 5, or 12-18.

In one aspect, the disclosure features a collection or library of saccharide structures, e.g., saccharide structures described herein, e.g., a monosaccharide, disaccharide or larger oligosaccharide described herein.

In one aspect, the disclosure features preparations, e.g., substantially purified preparations, e.g., pharmaceutical preparations, of one or more saccharide structure described herein, e.g., a monosaccharide, disaccharide or larger oligosaccharide described herein. Also within the disclosure are reaction mixtures having two or more of the saccharide structures described herein, e.g., a monosaccharide, disaccharide or larger oligosaccharide described herein.

In one aspect, disclosure features oligosaccharides (either singly or as collections or libraries) are provided as a plurality of substantially purified preparations. In an embodiment each partially purified preparation is free of substantial amounts of other protected oligosaccharides or of substantial amounts of other protected oligosaccharides of the same length. Also within the disclosure are reaction mixtures having two or more of the oligosaccharides described herein.

In one aspect, the disclosure features a method of analyzing an oligosaccharide, e.g., an oligosaccharide described herein, comprising:

providing a test oligosaccharide, e.g., an oligosaccharide described herein having a predetermined level or pattern of derivatization;

determining a property of said test oligosaccharide, thereby analyzing an oligosaccharide.

In one aspect, the disclosure features a method of identifying an oligosaccharide, e.g., an oligosaccharide described herein, that binds to a target protein, comprising:

providing a test oligosaccharide, a collection or a library of test oligosaccharides having a predetermined level of pattern of derivatization;

determining if the oligosaccharide or one or more of the oligosaccharide from the collection or library binds to a target polypeptide, to thereby identify an oligosaccharide that binds to the target polypeptide.

In one aspect, the disclosure features a database disposed on tangible medium that includes: at least 10 records wherein a record comprises, an identifier which identifies a saccharide structure disclosed herein; and optionally an identifier which identifies a biological or chemical property of the saccharide structure.

Aspects of the disclosure also include a system comprising: a user interface for inputting a query; a processor for generating a query result; a selector to select a parameter based on the sequence, a chemical or a biological property of a saccharide structure disclosed herein; and the database described above.

The invention allows for the production of oligosaccharide structures, e.g., a decasaccharide, having defined structure and/or properties. The invention provides for oligosaccharide drugs and drug candidates, e.g., drugs or drug candidates having a desired biological property, e.g., anti-factor IIa activity, anti-factor Xa activity, anti-thrombotic activity, anti-inflammatory activity, anti-angiogenic activity, anti-cancer or anti-metastatic activity. Preparations of the oligosaccharides, e.g., preparations of oligosaccharide drugs, can have optimized heterogeneity and can, e.g., be less heterogeneous than oligosaccharide drugs prepared from natural sources. The invention also provides libraries and other constructs useful for the production of oligosaccharides.

DETAILED DESCRIPTION

Figure 1:
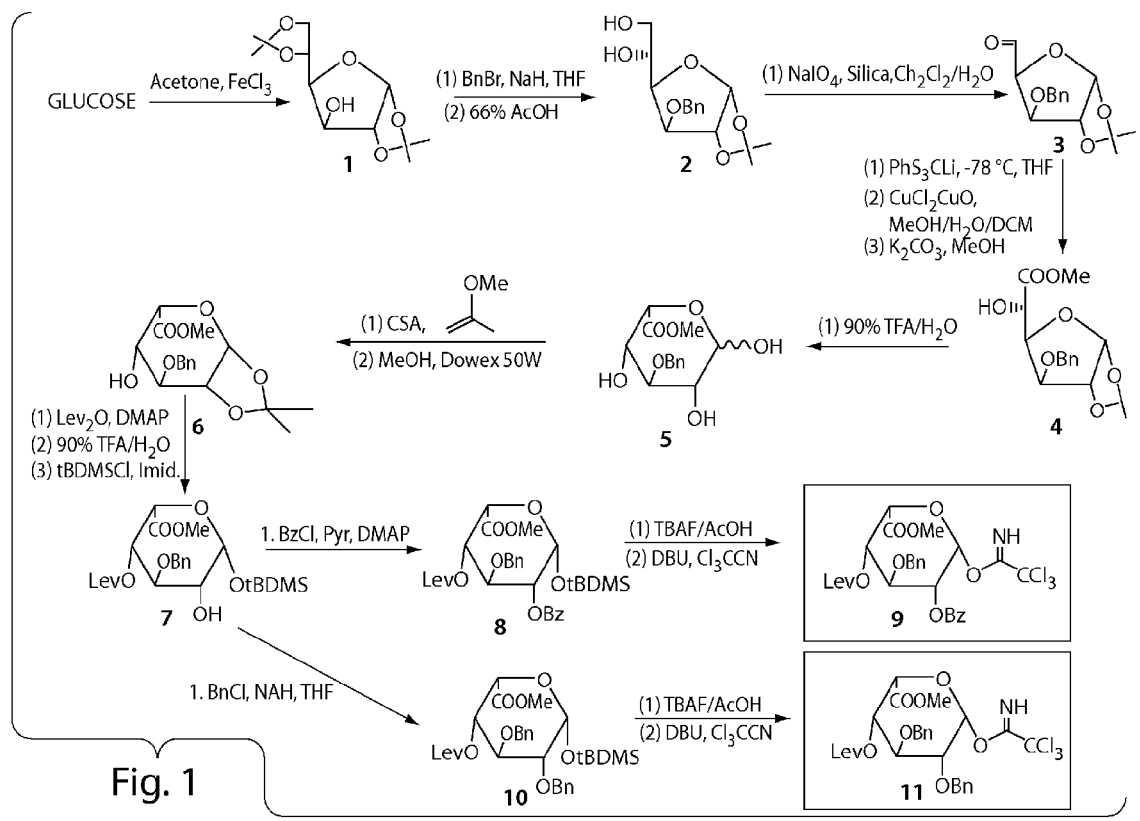
FIG. 1 depicts synthesis of an iduronic acid having a first protecting group that allows derivatization or does not allow for derivatization (10) and an iduronic acid that has a first protecting group that allows for derivatization and a second protecting group that does not allow for derivatization (8).

Described in the present disclosure are oligosaccharides that are a disaccharide or larger that provide a scaffold for making oligosaccharides having a sequence with a preselected pattern of substituents, e.g., sulfates, acetates, and hydrogen, at positions within the oligosaccharide that are amendable to derivatization. These oligosaccharides allow the design and synthesis of oligosaccharide structures having preselected complex patterns of derivatization, e.g., preselected complex patterns of sulfation or acetylation. In some embodiments, the oligosaccharide has only two or three different protecting groups. At least two of the protecting groups have different reactivities. One protecting group is replaced to a first degree, e.g., substantially completely replaced, with a derivatizing group under selected conditions. The other protecting group is replaced to a second degree, usually relatively less, e.g., it gives substantially no derivatization, under the same conditions.

In other embodiments, the positions amenable to derivatization within a disaccharide or a disaccharide of a larger oligosaccharide are all distinct from one another or a subset of the positions amendable to derivatization within the disaccharide are distinct from one another, e.g., three or more of these positions are distinct from each other. In one embodiment, the positions amendable to derivatization within a disaccharide are orthogonal protecting groups and thus, each protecting group is selected such that any one can be individually removed, without removing the others, to allow reaction of the protected position with another moiety, e.g., to result in the placement of a substituent, e.g., a sulfate, acetate or hydrogen, at the protected moiety. These oligosaccharides allow for placement of a particular substituent at particular positions with an oligosaccharide.

Also described in the present disclosure are monosaccharides that can be used, e.g., to make oligosaccharide structures having protecting groups at positions amenable to derivatization, methods of making a saccharide structure described herein, e.g., a monosaccharide, disaccharide or larger oligosaccharide described herein. Collections and libraries of a saccharide structure, e.g., a monosaccharide, disaccharide or larger oligosaccharide described herein, kits, reaction mixtures, and compositions are described herein. Furthermore, methods of analyzing an oligosaccharide described herein, are provided.

Methods, compounds and compositions described herein can use, or be made with, two protecting groups. The two protecting groups can, and usually will, have substantially different reactivities (the ability to be replaced with a derivative) under a given set of conditions. In most cases one protecting group will be replaced to a substantially greater degree than the other under a selected condition. In embodiments the other protecting group will be substantially more reactive under a second set of conditions. In some embodiments one protecting group will be substantially completely replaced under a selected condition and the other protecting group will be substantially unreacted (not replaced) under those conditions. In embodiments both groups will be reactive, either to the same degree, or more commonly, to different degrees, under a selected condition. The latter relationship is useful, e.g., in making libraries, e.g., combinatorial libraries, or in dirty synthesis.

The term "substituent" as used herein refers to any moiety naturally associated with an oligosaccharide at a position amendable to derivatization. For example, the substituent is a sulfate, an acetate or a hydrogen.

Positions amendable to derivatization include any position on a saccharide structure that can have a sulfate or acetate associated with that position. Positions involved with linking one saccharide structure to another are not encompassed by this term.

The term "derivatization" includes sulfation and acetylation but does not include hydrogenation and linkage of saccharide structures to each other.

A "collection" as used herein means more than one and less than ten members. For example, a collection can be 2, 3, 4, 5, 6, 7, 8 or 9 monosaccharides or oligosaccharides.

The term "library" as used herein refers to 10 or more members. For example, a library can include at least 10, 15, 20, 25, 30, 35, 40, 45, 50, 55, 60, 65, 70, 75, 80, 85, 90, 95, 100, 500, or 1,000 monosaccharides or oligosaccharides.

Monosaccharide Synthesis

Described herein are monosaccharides having a protecting group at each position in the monosaccharide amenable to derivatization. These are useful, e.g., for providing disaccharides or larger oligosaccharides, or libraries thereof, having preselected sequences and/or levels or patterns of derivatization, e.g., sulfation or acetylation.

In some aspects, the protecting group at any given position can be a first protecting group that allows derivatization, e.g., sulfation or acetylation, or a second protecting group that does not allow derivatization, e.g., sulfation or acetylation. The identity of each protecting group at positions amendable to derivatization can independent of the protecting group at any other position amendable to derivatization.

Figure 2:
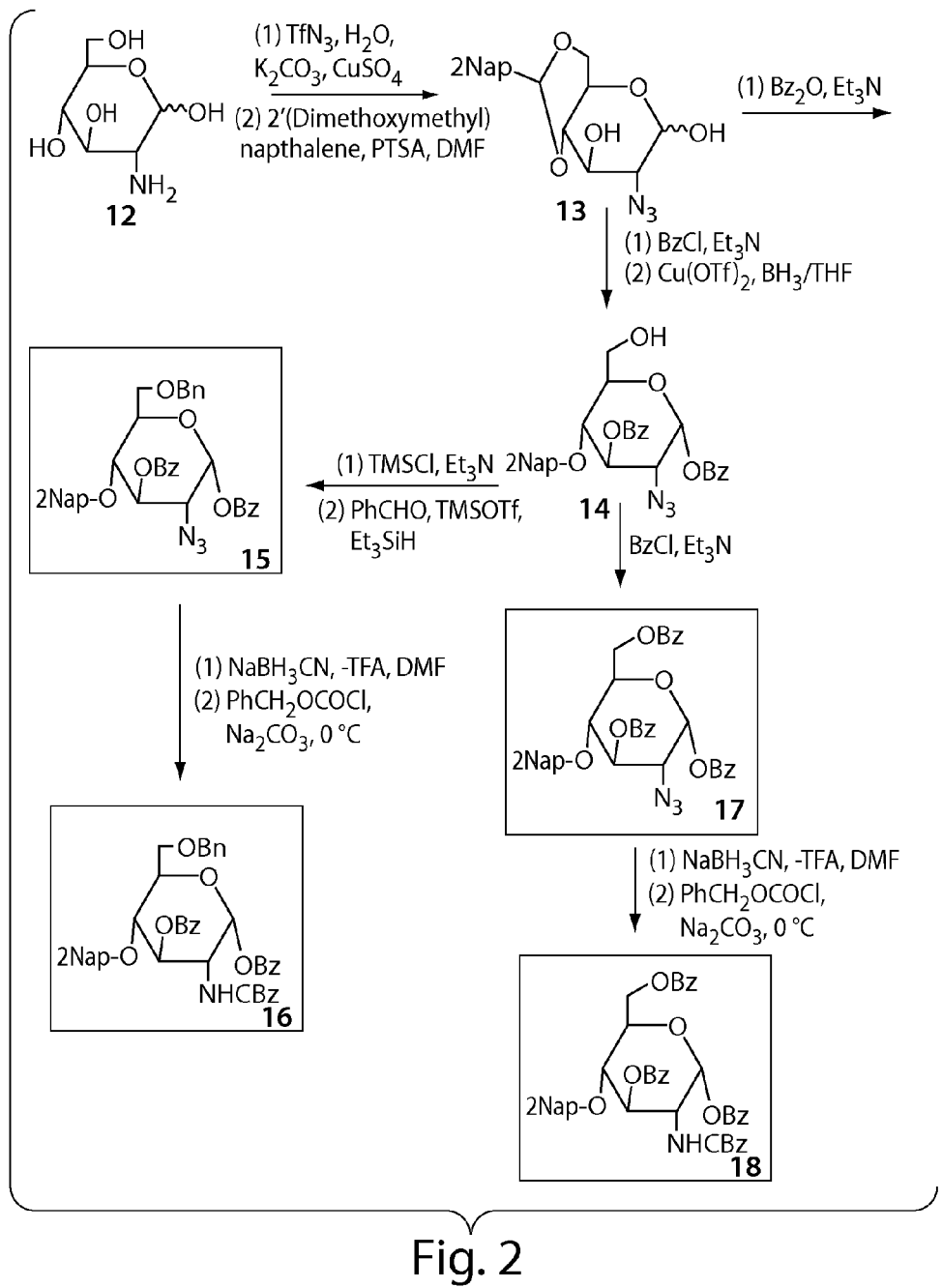
FIG. 2 depicts synthesis of a glucosamine having a first protecting group that allows derivatization or does not allow for derivatization (17, 18, 23 and 24) and a glucosamine that has a first protecting group that allows for derivatization and a second protecting group that does not allow for derivatization (15, 16, 21 and 22).
Figure 2:
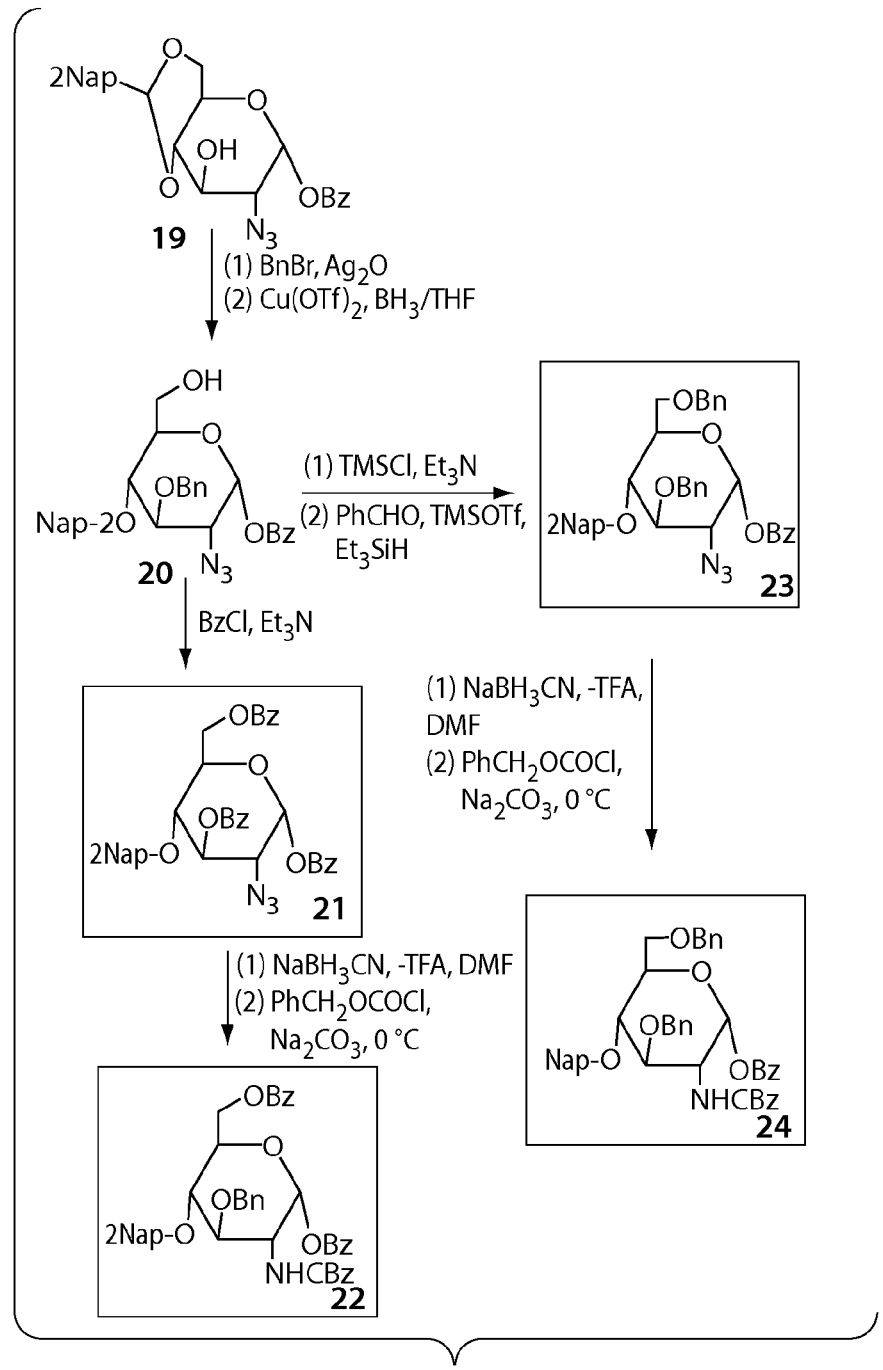
Figure 3:
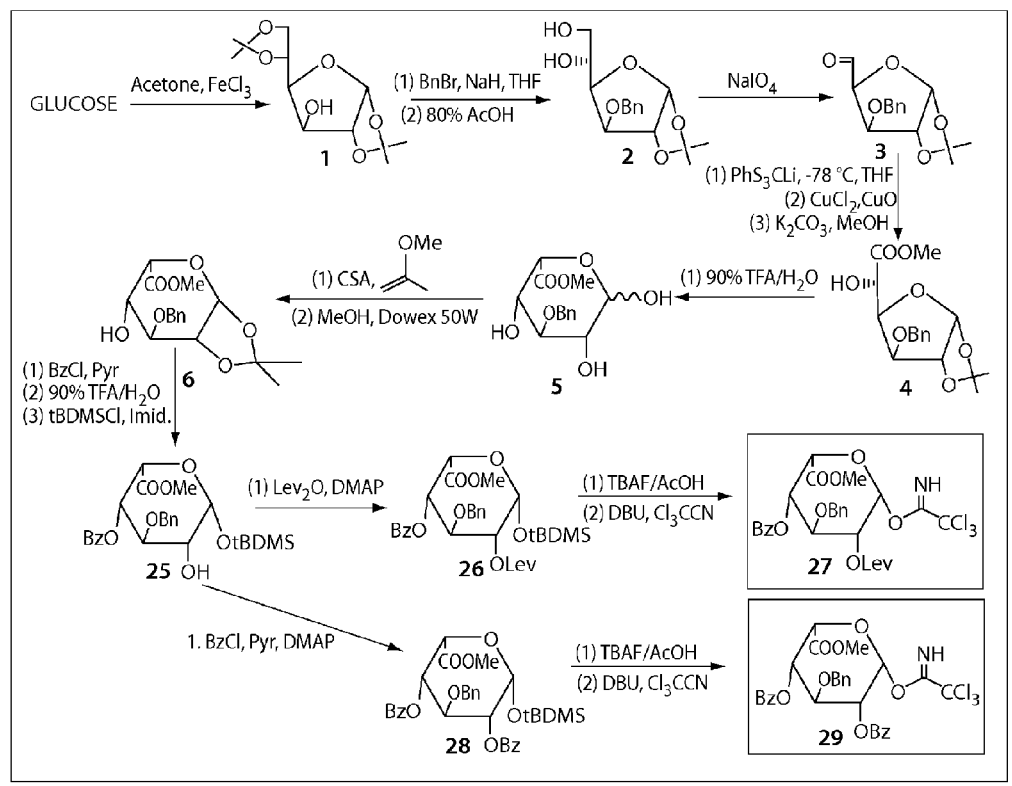
FIG. 3 depicts synthesis of a diversely protected iduronic acid having orthogonal protecting groups of a Lev at C-2 in Compound 26 and a Bz at C-2 in Compound 28.
Figure 4:
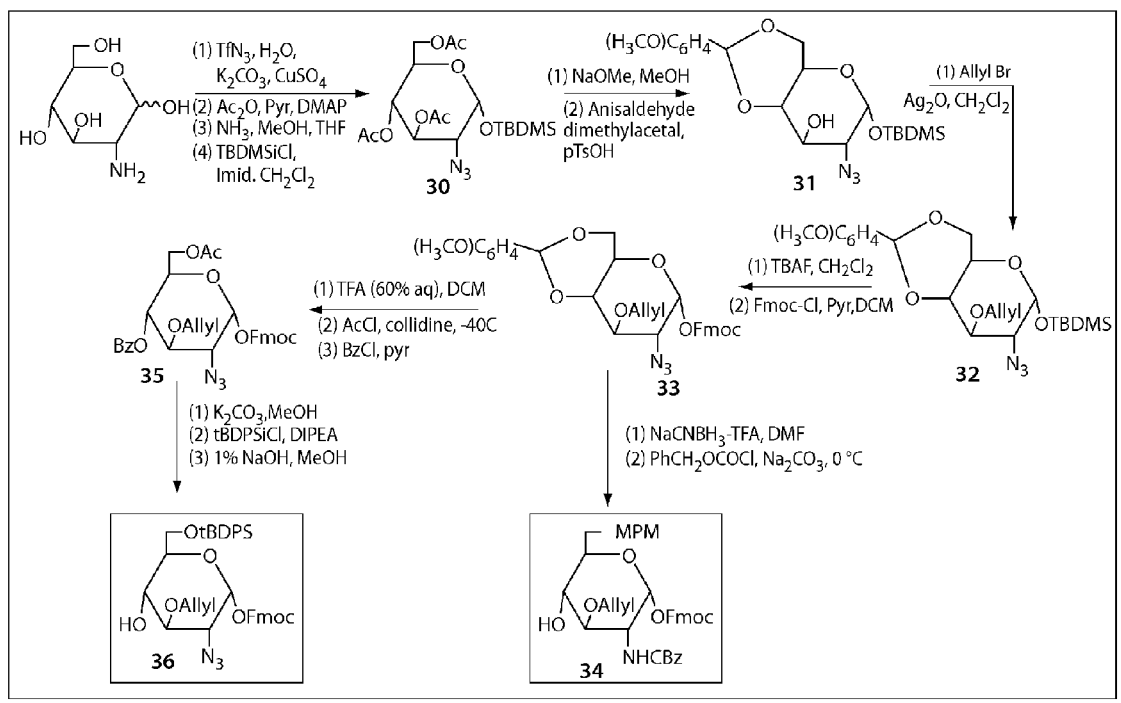
FIG. 4 depicts synthesis of a diversely protected glucosamine having orthogonal protecting groups of a tBDPS in Compound 36 and MPM in Compound 34; and an azide in Compound 36 and a benzyl carbamate NHCBz in Compound 34.
Figure 5:
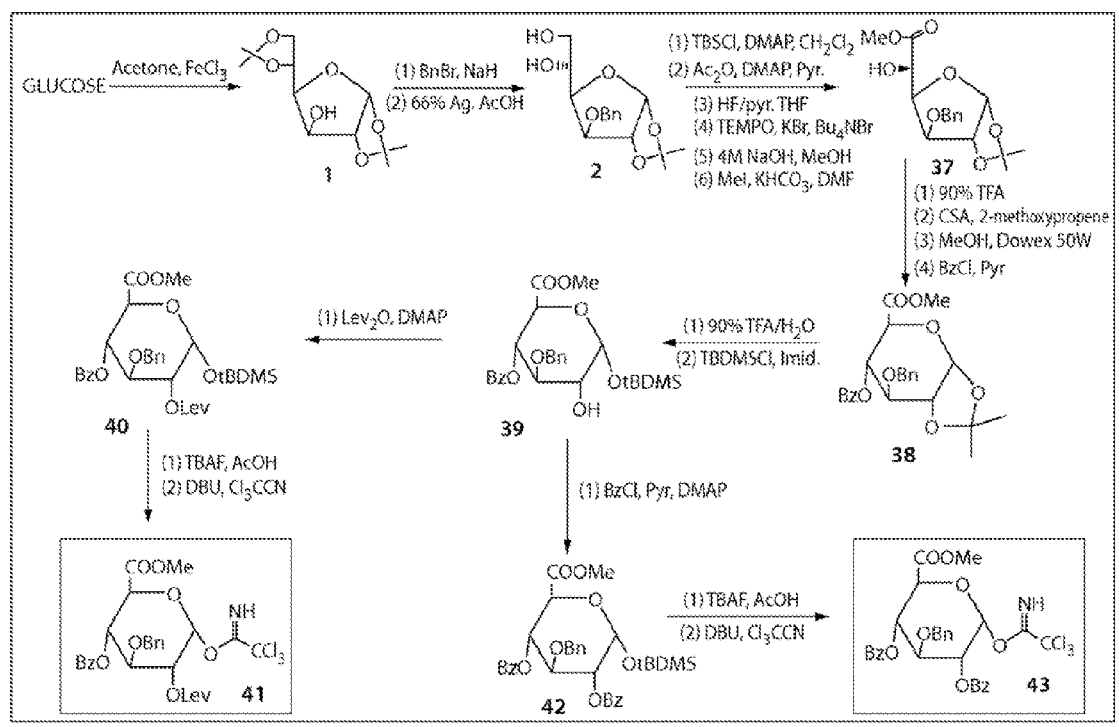
FIG. 5 depicts synthesis of a diversely protected glucuronic acid having orthogonal protecting groups of a Lev at C-2 in Compound 40 and a Bz at C-2 in Compound 42.
Figure 6:
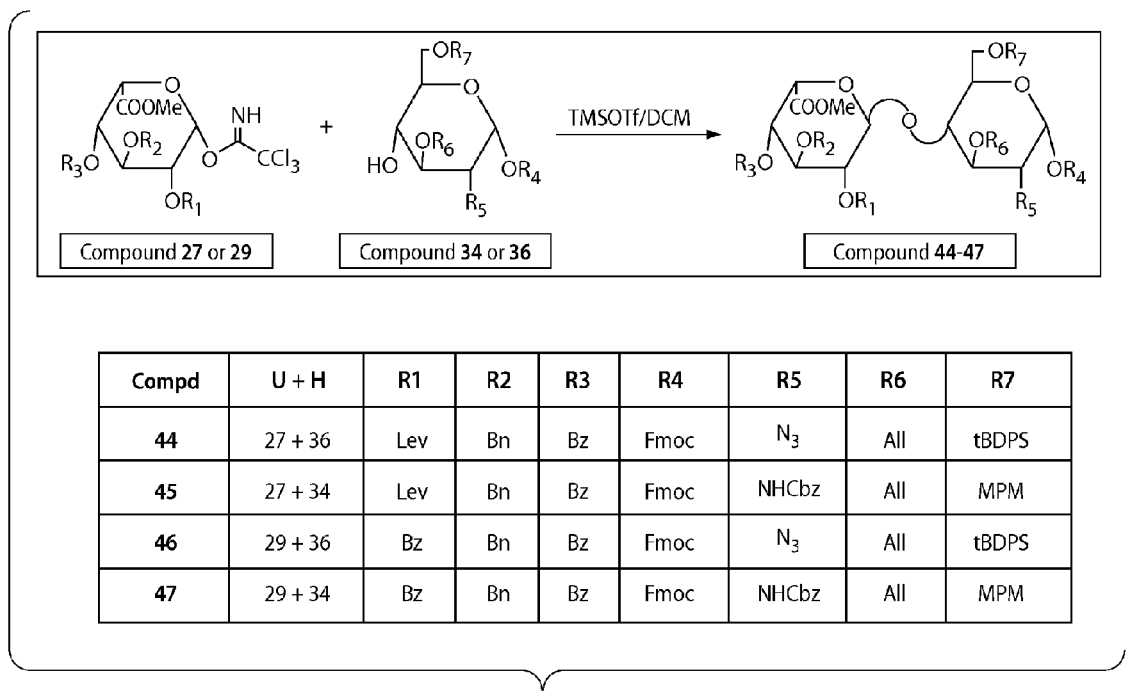
FIG. 6 depicts the synthesis of various diversely protected disaccharides by various combinations of diversely protected monosaccharides of iduronic acid and glucosamine.
Figure 7:
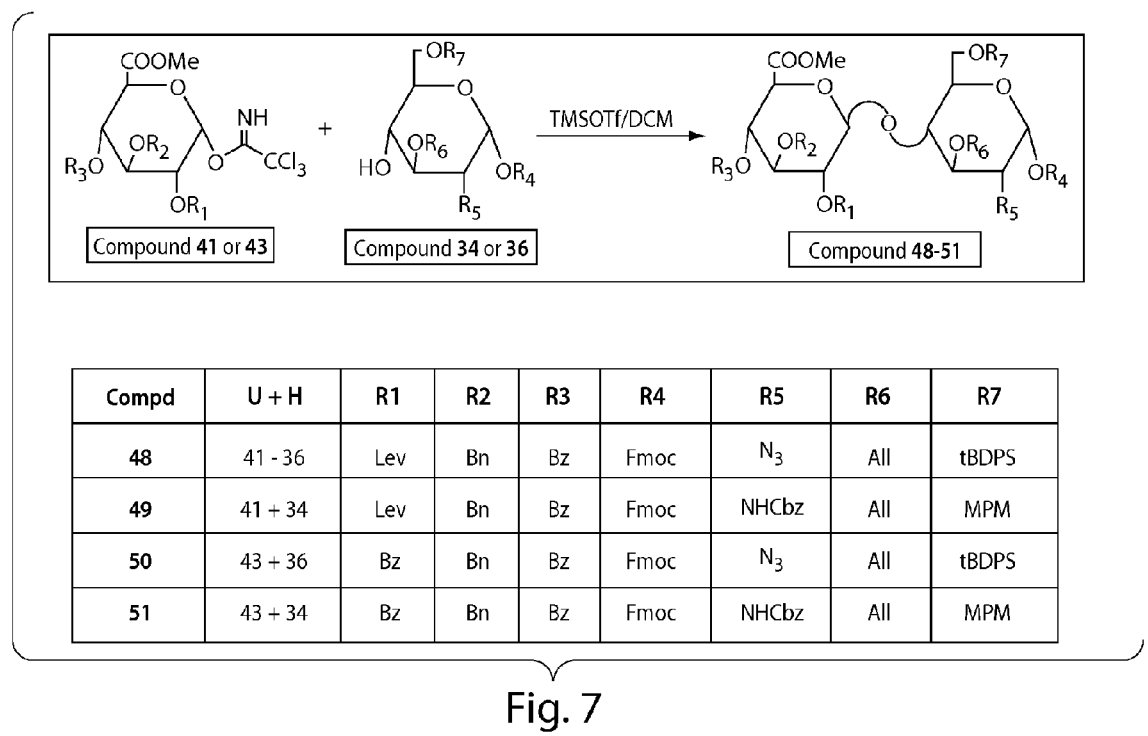
FIG. 7 depicts the synthesis of various diversely protected disaccharides by various combinations of diversely protected monosaccharides of glucuronic acid and glucosamine.
Figure 8:
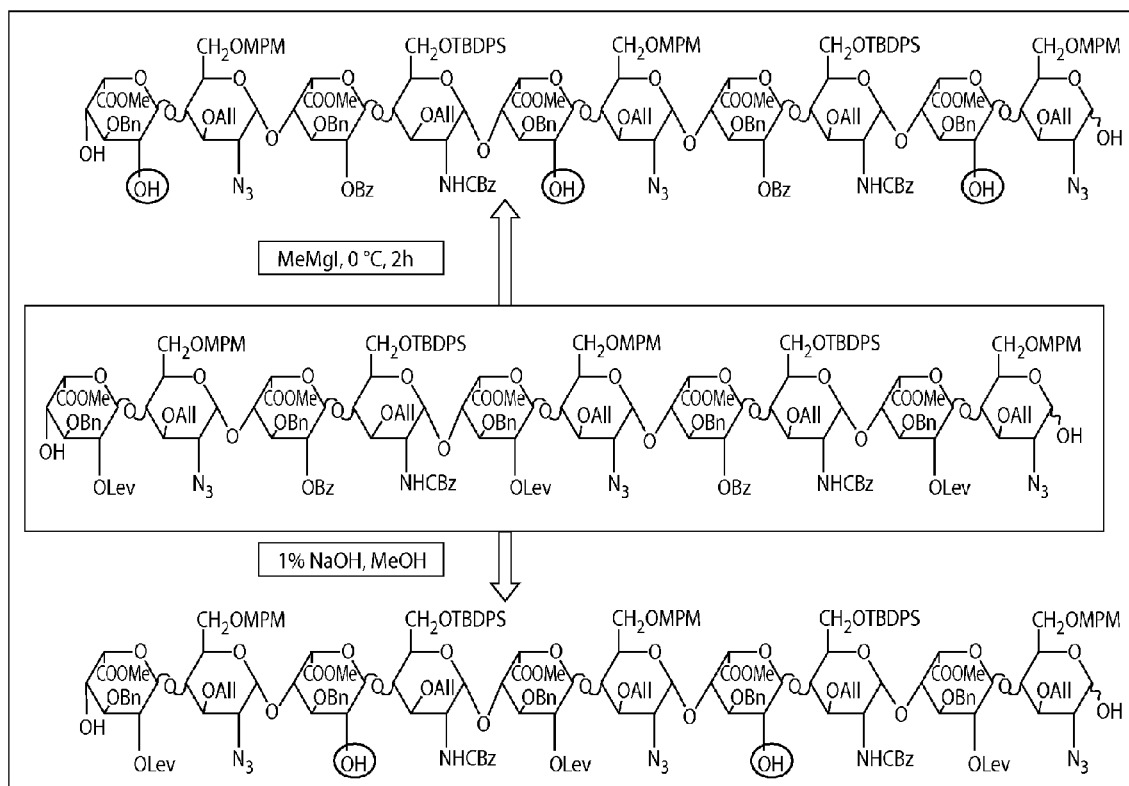
FIG. 8 shows a diversely protected decasaccharide having a preselected sequence and different conditions for deprotecting and adding substituents at C-2 of iduronic acid within the diversely protected decasaccharide.
Figure 9:
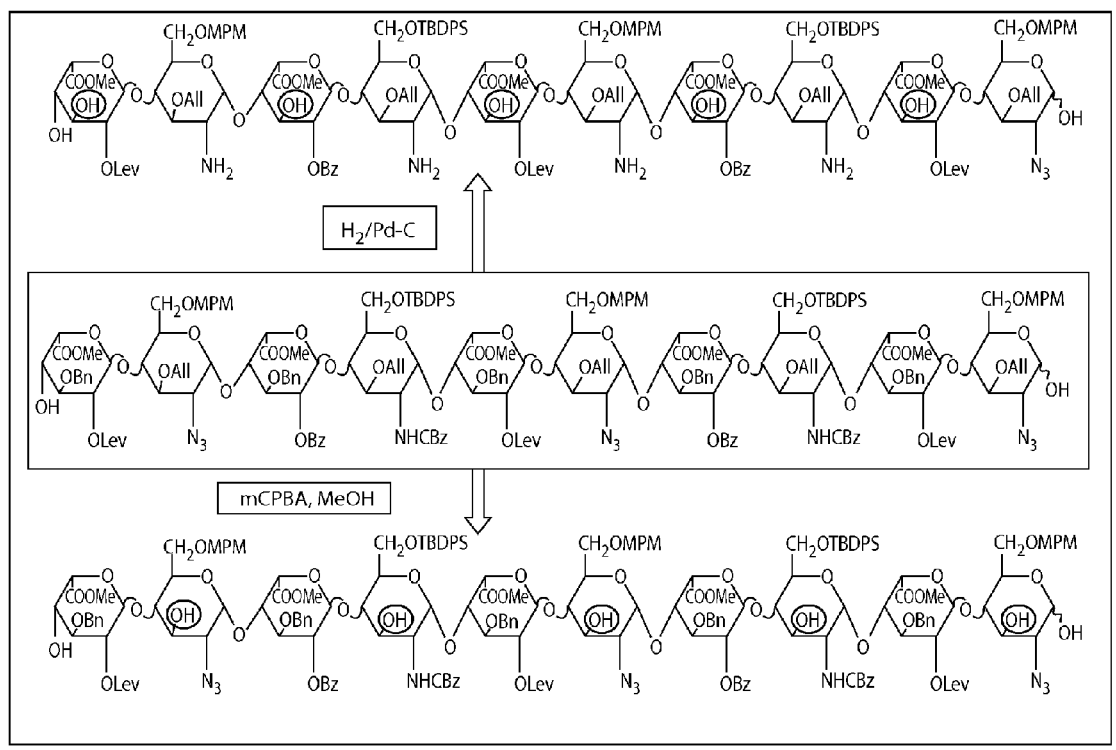
FIG. 9 shows a diversely protected decasaccharide having a preselected sequence and different conditions for deprotecting and adding substituents at C-3 of Glucosamine/and Iduronic acid residues within the diversely protected decasaccharide.
Figure 10:
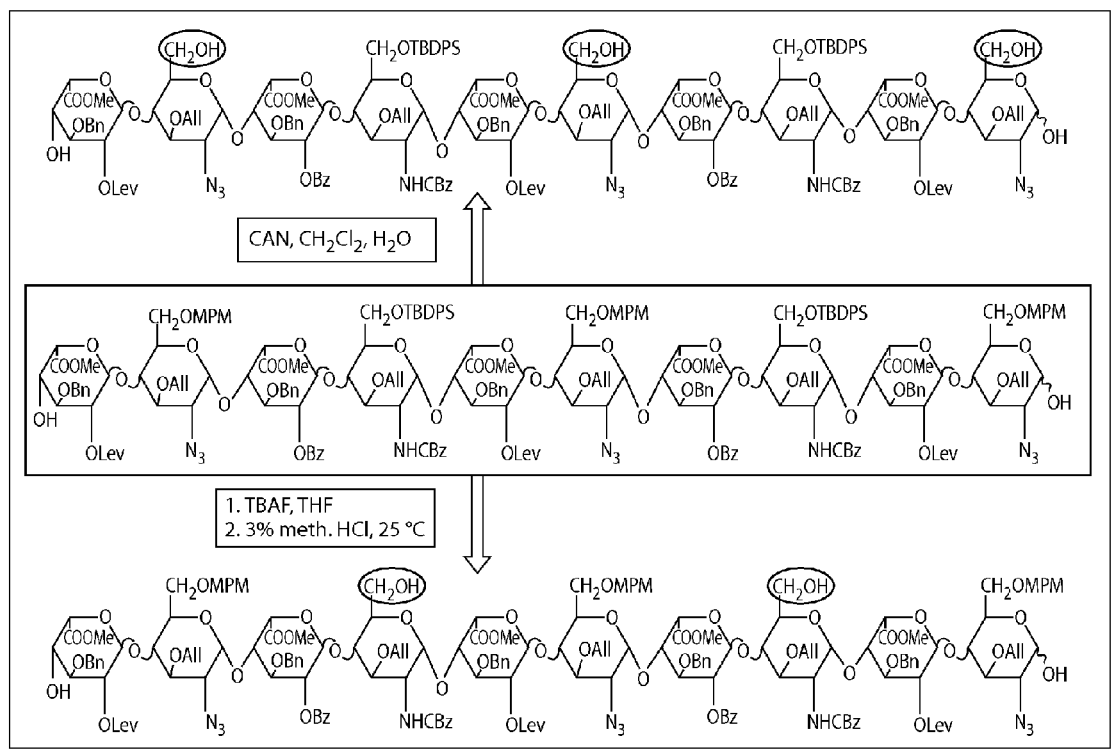
FIG. 10 shows a diversely protected decasaccharide having a preselected sequence and different conditions for deprotecting and adding substituents at C-6 of glucosamine residues within the diversely protected decasaccharide.
Figure 11:
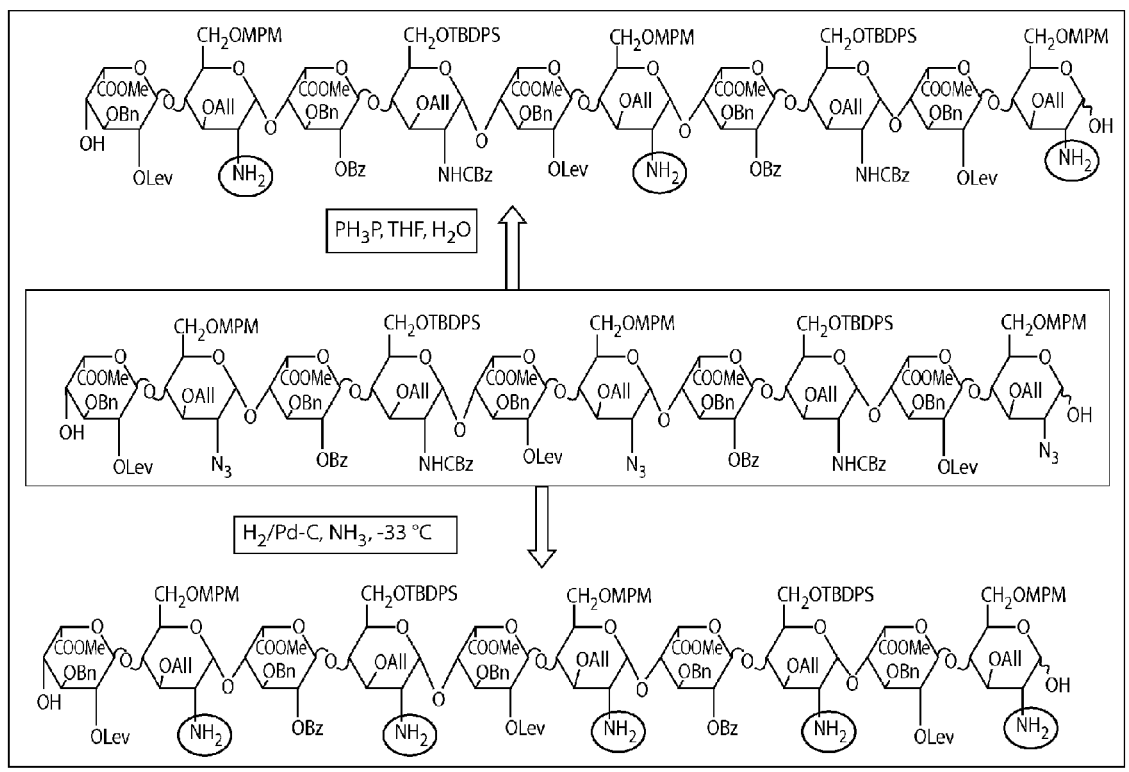
FIG. 11 shows a diversely protected decasaccharide having a preselected sequence and different conditions for deprotecting and adding substituents at C-2 of glucosamine residues within the diversely protected decasaccharide.

Examples of such monosaccharides are provided in FIGS. 1 and 2. In addition, examples of methods of synthesizing these monosaccharides are provided in FIGS. 1 and 2. Known methods can be used to make other monosaccharides, e.g., monosaccharides described herein.

In other embodiments, diversely protected monosaccharides are described. A diversely protected monosaccharide refers to a monosaccharide having each protecting group or more than two protecting groups of the monosaccharide that are orthogonal protecting groups and thus, each protecting group, or a subset of the protecting groups (i.e., more than two protecting groups within a monosaccharide) is selected such that any one can be individually removed, without removing the others, to allow reaction of the protected position with another moiety, e.g., to result in the placement of a substituent, e.g., a sulfate, acetate or a hydrogen, at the protected moiety.

Examples of diversely protected monosaccharides are provided in FIGS. 3-5, 12 and 13. FIGS. 3-5, 12 and 13 also describe exemplary methods of synthesizing these diversely protected monosaccharides. Known methods can be used to make other monosaccharides, e.g., other monosaccharides described herein Disaccharide Synthesis The disclosure also provides disaccharides having a protecting group at each position in the disaccharide amenable to derivatization. The protecting group at any given position can be a first protecting group that allows derivatization, e.g., sulfation or acetylation, or a second protecting group that does not allow derivatization, e.g., sulfation or acetylation. These disaccharides can be made by combining monosaccharides having protecting groups at positions amendable to derivatization with each other to form a disaccharide. In one aspect, various combinations of protected monosaccharides, e.g., the protected monosaccharides described herein, can be made to form a collection or library of protected disaccharides.

A disaccharide, e.g., a disaccharide described herein, can be made using a standard TMSOTf-mediated coupling of one protected monosaccharide to another protected monosaccharide. For example, an uronic acid trichloroacetimidate donor and a glucosamine acceptor can be coupled to one another using known TMSOTf-coupling techniques. Such techniques are described in Lohman et. al. (2004) *J. Org. Chem.* 69(12), 4081-4093.

In some embodiments, the disaccharide can have only two or three different protecting groups. The two or at least two of the three protecting groups have different reactivities. One protecting group is replaced to a first degree, e.g., substantially completely replaced or completely, with a derivatizing group under selected conditions. This protecting group is referred to herein as "a protecting group that allows derivatization". The other protecting group gives relatively less, e.g., it gives substantially no derivatization or no derivatization, under the same conditions. This protecting group is referred to herein as "a protecting group that does not allow derivatization". It should be noted that if the reactive conditions are changed, a protecting group that allows derivatization under one set of conditions can be a protecting group that does not allow derivatization under another set of conditions.

The protecting groups can be selected from known protecting groups such as the protecting groups described herein.

Table I and schematic A provided below exemplify various disaccharides that can be produced by coupling monosaccharides protected with various combinations of a protecting group that allows derivatization (e.g., benzoyl and/or a benzoyl containing group) and monosaccharides protected by a protecting group that does not allow derivatization (e.g., benzyl and/or azide). Monosaccharides are referred to in Table I as AA, AB and BB. The disaccharides are an uronic acid (iduronic acid) coupled to a hexosamine (glucosamine). However, it should be understood that other combinations, for example, a glucuronic acid and a glucosamine, can be produced using the same methodology. The disaccharides exemplified are various combinations of the monosaccharides AA, AB and BB. For uronic acid, A is a benzoyl protecting group that allows derivatization, e.g., when derivatized, the benzoyl will be replaced with $SO_3$—, and B is a benzyl protecting group that does not allow derivatization, e.g., the benzyl will be replaced with a hydrogen. For glucosamine, at positions $R_6$ and $R_7$, A represents a benzoyl protecting group that allows derivatization, e.g., when derivatized, the benzoyl will be replaced with $SO_3$—, and B represents a benzyl protecting group that does not allow derivatization, e.g., the benzyl will be replaced with a hydrogen. For position $R_5$ of glucosamine, A represents a benzoyl containing group, NHCBz, as the protecting group that allows derivatization, e.g., when derivatized, the benzoyl containing group will be replaced with $NHSO_3$—, and B represents an azide protecting group that does not allow derivatization, e.g., the azide will be replaced with $NH_2$.

Schematic A:

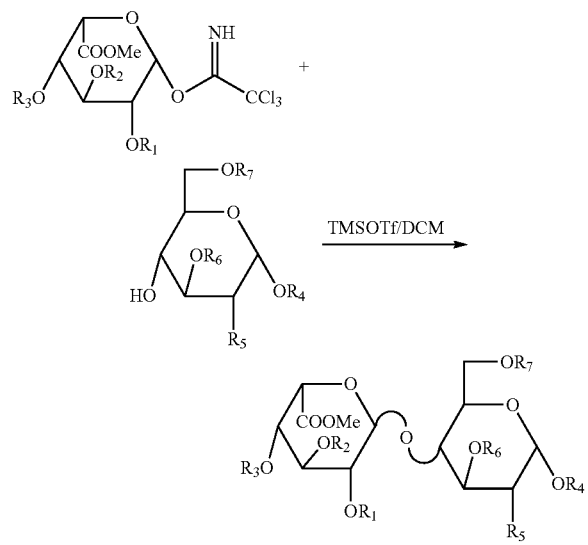

Table I provides various combinations of disaccharides that have protecting groups at positions within the monosaccharides (the glucuronic acid and glucosamine) amendable to derivatization. The disaccharide code denotes the relevant substituents in the order $R^1$-$R^7$-$R^6$-$R^5$.

TABLE I

Exemplary Uronic Acid-Hexosamine Disaccharides

| Disacc. Code | R1 | R2 | R3 | R4 | R5 | R6 | R7 | U + H |
|---|---|---|---|---|---|---|---|---|
| 1 AAAB | Bz | Bn | Lev | Bz | N3 | Bz | Bz | 9 + 17 |
| 2 AAAA | Bz | Bn | Lev | Bz | NHCBz | Bz | Bz | 9 + 18 |
| 3 BAAB | Bn | Bn | Lev | Bz | N3 | Bz | Bz | 11 + 17 |
| 4 BAAA | Bn | Bn | Lev | Bz | NHCBz | Bz | Bz | 11 + 18 |
| 5 ABAB | Bz | Bn | Lev | Bz | N3 | Bz | Bn | 9 + 15 |
| 6 ABAA | Bz | Bn | Lev | Bz | NHCBz | Bz | Bn | 9 + 16 |
| 7 AABB | Bz | Bn | Lev | Bz | N3 | Bn | Bz | 9 + 21 |
| 8 AABA | Bz | Bn | Lev | Bz | NHCBz | Bn | Bz | 9 + 22 |
| 9 BBAB | Bn | Bn | Lev | Bz | N3 | Bz | Bn | 11 + 15 |
| 10 BBAA | Bn | Bn | Lev | Bz | NHCBz | Bz | Bn | 11 + 16 |

TABLE I-continued

Exemplary Uronic Acid-Hexosamine Disaccharides

| Disacc. Code | R1 | R2 | R3 | R4 | R5 | R6 | R7 | U + H |
|---|---|---|---|---|---|---|---|---|
| 11 ABBB | Bz | Bn | Lev | Bz | N3 | Bn | Bn | 9 + 23 |
| 12 ABBA | Bz | Bn | Lev | Bz | NHCBz | Bn | Bn | 9 + 24 |
| 13 BBBB | Bn | Bn | Lev | Bz | N3 | Bn | Bn | 11 + 23 |
| 14 BBBA | Bn | Bn | Lev | Bz | NHCBz | Bn | Bn | 11 + 24 |
| 15 BABB | Bn | Bn | Lev | Bz | N3 | Bn | Bz | 11 + 21 |
| 16 BABA | Bn | Bn | Lev | Bz | NHCBz | Bn | Bz | 11 + 22 |

Table II and schematic B provided below exemplify additional disaccharides that can be produced by coupling monosaccharides protected with various combinations of a protecting group that allows derivatization (e.g., benzoyl or a benzoyl containing group) and monosaccharides protected by a protecting group that does not allow derivatization (e.g., benzyl or azide). Monosaccharides are referred to in Table II as AA, AB and BB. The disaccharides are a hexosamine (glucosamine) coupled to an uronic acid (iduronic acid). However, it should be understood that other combinations, for example, a glucosamine coupled to a glucuronic acid, can be produced using the same methodology. The disaccharides exemplified are various combinations of the monosaccharides AA, AB and BB. For glucosamine, at positions $R_6$ and $R_7$, A represents a benzoyl protecting group that allows derivatization, e.g., when derivatized, the benzoyl will be replaced with $SO_3$—, and B represents a benzyl protecting group that does not allow derivatization, e.g., the benzyl will be replaced with a hydrogen. For position $R_5$ of glucosamine, A represents a benzoyl containing group, NHCBz, as the protecting group that allows derivatization, e.g., when derivatized, the benzoyl containing group will be replaced with $NHSO_3$—, and B represents an azide protecting group that does not allow derivatization, e.g., the azide will be replaced with $NH_2$. For uronic acid, A is a benzoyl protecting group that allows derivatization, e.g., when derivatized, the benzoyl will be replaced with $SO_3$—, and B is a benzyl protecting group that does not allow derivatization, e.g., the benzyl will be replaced with a hydrogen.

Schematic B:

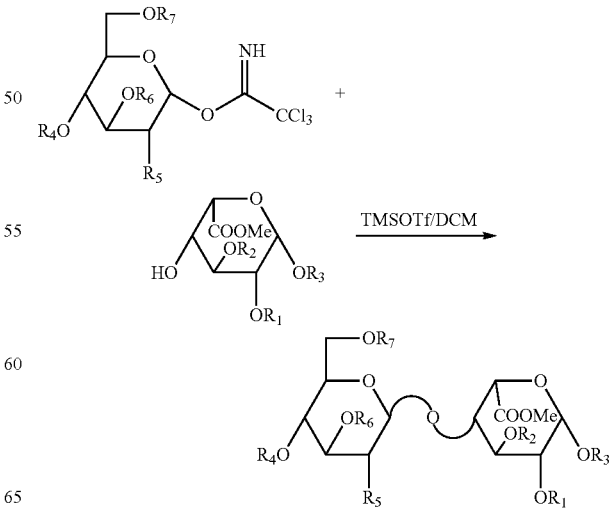

TABLE II

Exemplary Hexosamine-Uronic Acid Disaccharides

| Disacc. Code | | R1 | R2 | R3 | R4 | R5 | R6 | R7 | H + U |
|---|---|---|---|---|---|---|---|---|---|
| 1 | AAAB | Bz | Bn | tBDMS | 2-Nap | N$_3$ | Bz | Bz | 17 + 8 |
| 2 | AAAA | Bz | Bn | tBDMS | 2-Nap | NHCBz | Bz | Bz | 18 + 8 |
| 3 | BAAB | Bn | Bn | tBDMS | 2-Nap | N$_3$ | Bz | Bz | 17 + 10 |
| 4 | BAAA | Bn | Bn | tBDMS | 2-Nap | NHCBz | Bz | Bz | 18 + 10 |
| 5 | ABAB | Bz | Bn | tBDMS | 2-Nap | N$_3$ | Bz | Bn | 15 + 8 |
| 6 | ABAA | Bz | Bn | tBDMS | 2-Nap | NHCBz | Bz | Bn | 16 + 8 |
| 7 | AABB | Bz | Bn | tBDMS | 2-Nap | N$_3$ | Bn | Bz | 21 + 8 |
| 8 | AABA | Bz | Bn | tBDMS | 2-Nap | NHCBz | Bn | Bz | 22 + 8 |
| 9 | BBAB | Bn | Bn | tBDMS | 2-Nap | N$_3$ | Bz | Bn | 15 + 10 |
| 10 | BBAA | Bn | Bn | tBDMS | 2-Nap | NHCBz | Bz | Bn | 16 + 10 |
| 11 | ABBB | Bz | Bn | tBDMS | 2-Nap | N$_3$ | Bn | Bn | 23 + 8 |
| 12 | ABBA | Bz | Bn | tBDMS | 2-Nap | NHCBz | Bn | Bn | 24 + 8 |
| 13 | BBBB | Bn | Bn | tBDMS | 2-Nap | N$_3$ | Bn | Bn | 23 + 10 |
| 14 | BBBA | Bn | Bn | tBDMS | 2-Nap | NHCBz | Bn | Bn | 24 + 10 |
| 15 | BABB | Bn | Bn | tBDMS | 2-Nap | N$_3$ | Bn | Bz | 21 + 10 |
| 16 | BABA | Bn | Bn | tBDMS | 2-Nap | NHCBz | Bn | Bz | 22 + 10 |

As described elsewhere herein, these disaccharides are useful, for providing oligosaccharides, or libraries thereof, having preselected sequences and/or levels or patterns of derivatization, e.g., sulfation or acetylation.

Oligosaccharide Synthesis

The disclosure features oligosaccharides that can have a preselected sequence, e.g., a sequence of saccharide structures having a preselected pattern of derivatization. The oligosaccharide, e.g., an oligosaccharide described herein, allows the design and synthesis of oligosaccharide structures having preselected complex patterns of derivatization, e.g., preselected complex patterns of sulfation or acetylation. The oligosaccharide can be, e.g., a disaccharide, a trisaccharide, a tetrasaccharide, a pentasaccharide, a hexasaccharide, an octasaccharide, a decasaccharide, a dodecasaccharide, tetradecasaccharide, hexadecasaccharide, or octadecasaccharide.

In some embodiments, the oligosaccharide includes one or more disaccharide disclosed herein. Preferably, all of the disaccharide units of the oligosaccharide are disaccharide units which have a protecting group at all positions amendable to derivatization, e.g., all of the disaccharides of the oligosaccharide are a disaccharide described herein.

In some embodiments, the oligosaccharide can include a disaccharide or disaccharides having only two or three different protecting groups. The protecting group at any given position within the disaccharide or disaccharide can be a first protecting group that allows derivatization, e.g., sulfation or acetylation, or a second protecting group that does not allow derivatization, e.g., sulfation or acetylation. When the oligosaccharide includes more than one disaccharide unit described herein, the identity of a protecting group at any position within the disaccharide is independent of the identity of a protecting group in any other disaccharide of the oligosaccharide. The disaccharide can be, e.g., a disaccharide depicted in Table I, Table II, FIG. 6, FIG. 7, FIG. 14 or FIG. 15.

The protecting groups can be selected from known protecting groups such as the protecting groups described herein.

The oligosaccharide can be made by providing a first saccharide structure that is a monosaccharide or larger, e.g., the saccharide structure described herein, e.g., a disaccharide described herein; providing a second saccharide structure, e.g., the saccharide structure described herein, e.g., a disaccharide described herein, and attaching the first saccharide structure to the second saccharide structure. The method can also include attaching a third, fourth, fifth, sixth, seventh, etc. saccharide structure to make an oligosaccharide, e.g., an oligosaccharide having a preselected sequence. In one embodiment, the method includes providing a first disaccharide structure, e.g., a disaccharide described herein; attaching a second disaccharide structure, e.g., a disaccharide structure described herein, to the first disaccharide structure to provide a first tetrasaccharide structure; providing a third disaccharide structure, e.g., a disaccharide described herein; attaching a fourth disaccharide structure, e.g., a disaccharide structure described herein, to the third disaccharide structure to provide a second tetrasaccharide structure; attaching the first tetrasaccharide structure to the second tetrasaccharide structure to provide an octasaccharide structure; and attaching a fifth disaccharide structure, e.g., a disaccharide structure described herein, to the octasaccharide structure to thereby provide a decasaccharide structure. This is one example of how an oligosaccharide can be made. However, saccharide structures can be assembled by alternative methods. For example, a first disaccharide structure can be attached to a second disaccharide structure to form a tetrasaccharide. A third disaccharide can be attached to the tetrasaccharide to provide a hexasaccharide. A fourth disaccharide can be attached to the hexasaccharide to form an octasaccharide and a fifth disaccharide can be attached to the octasaccharide to form a decasaccharide.

Figure 16:
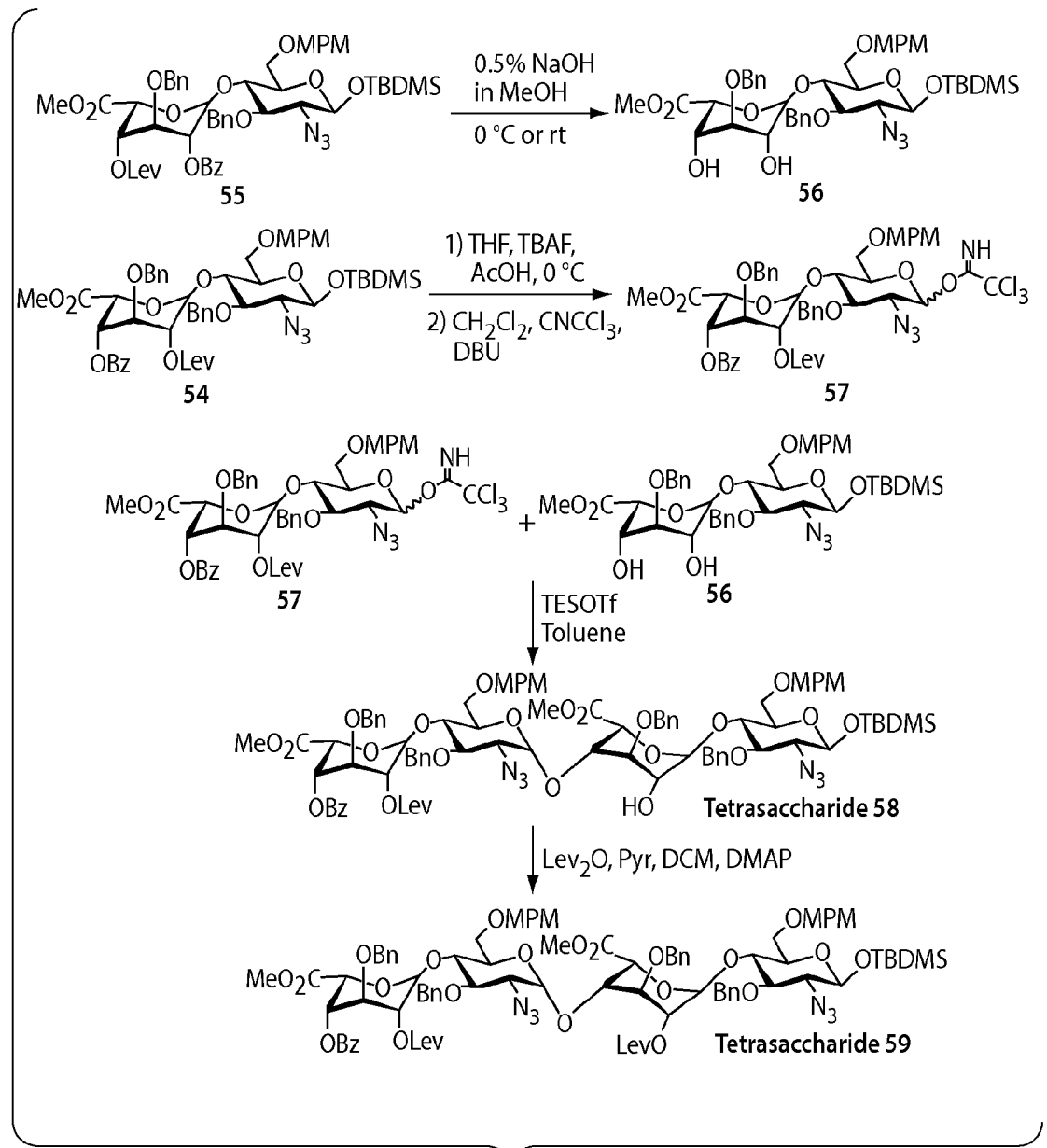
FIG. 16 depicts the synthesis of a diversely protected tetrasaccharide.
Figure 17:
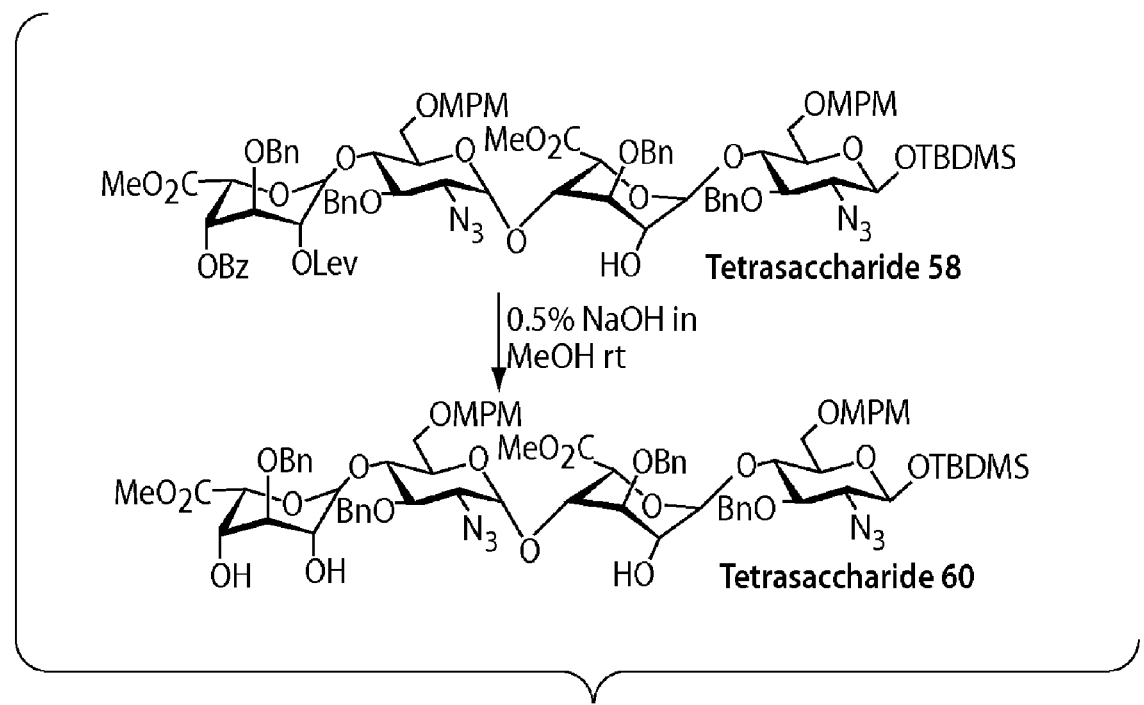
FIG. 17 depicts the synthesis of a diversely protected hexasaccharide.
Figure 17:
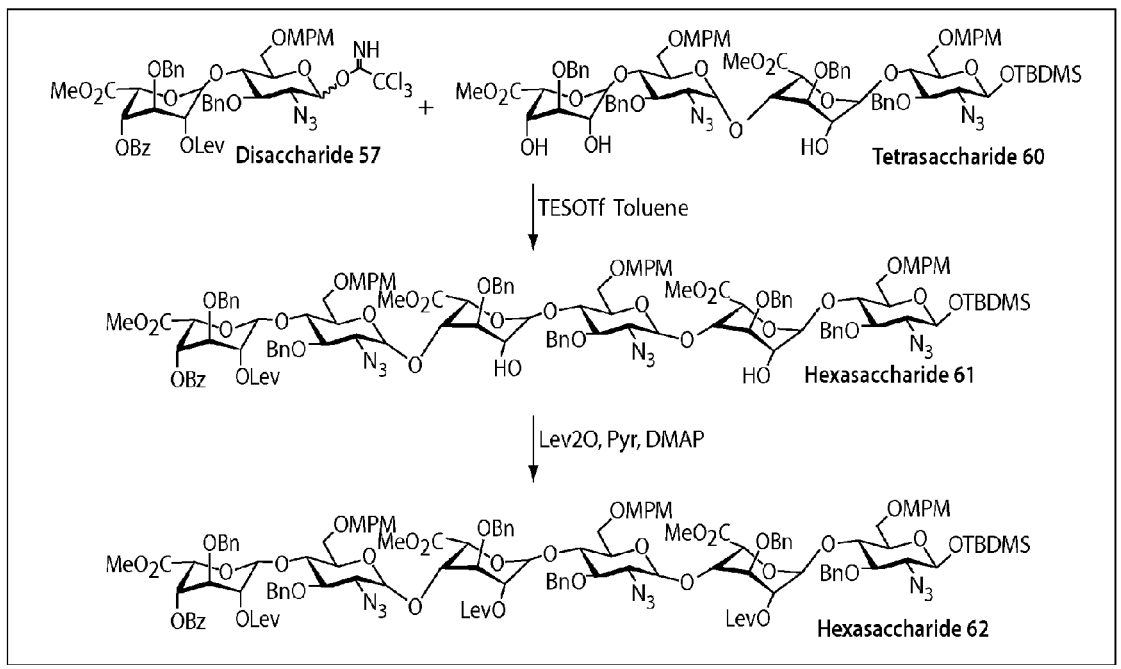

The methods for producing an oligosaccharide include the methods depicted in FIG. 16 and/or FIG. 17.

The saccharide structures can be attached to one another using a standard TMSOTf-mediated coupling of one protected monosaccharide to another protected monosaccharide. For example, an uronic acid trichloroacetimidate donor and a glucosamine acceptor can be coupled to one another using known TMSOTf-coupling techniques. Such techniques are described in Lohman et. al. (2004) *J. Org. Chem.* 69(12), 4081-4093.

The saccharide structures used to assemble an oligosaccharide, e.g., an oligosaccharide described herein, can include one or more protecting groups at a position within the saccharide structure that forms linkages with another saccharide structure. This position can be deprotected and the saccharide structures can be linked through this position of the saccharide structure using, e.g., TMSOTf or TESOTf-coupling.

The following is an example of a method of assembling various saccharide structures to prepare a protected oligosaccharide having a sequence that allows for a preselected pattern of derivatization. In this example, disaccharides 1, 2, 3 and 4 from Table I above are used. However, it is understood that any combination of disaccharides, e.g., any combination of the disaccharides depicted in Table I or Table II, can be used to make an oligosaccharide. Disaccharides 1, 2, 3 and 4 of Table I have the following structures:

1. (also referred to in Table I as AAAB)

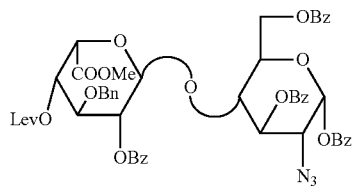

2. (also referred to in Table I as AAAA)

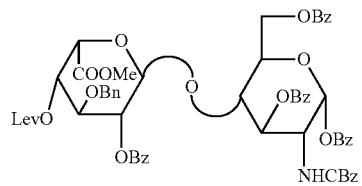

4. (also referred to in Table I as BAAA)

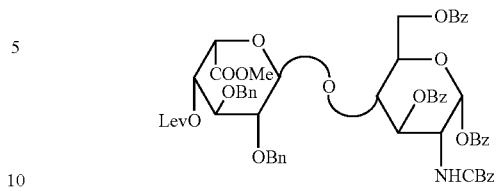

3. (also referred to in Table I as BAAB)

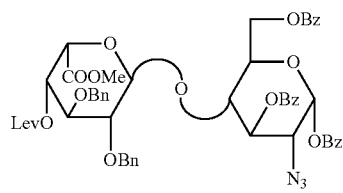

Disaccharides 1, 2, 3 and 4 can then be linked together in various combinations to provide oligosaccharides having a sequence with different patterns for derivatization. To exemplify this concept, three different decasaccharides are described below that are different combinations of the four disaccharides. The disaccharides are linked together by deprotecting the levulinoyl at position R3 and the benzoyl at position R4, and coupling the disaccharide structures to one another using TMSOTf-coupling as described in Lohman et. al. *J. Org. Chem.* 2004, 69(12), 4081-4093.

The following structure (i) is a combination of the following disaccharides: 1-2-3-4-1:

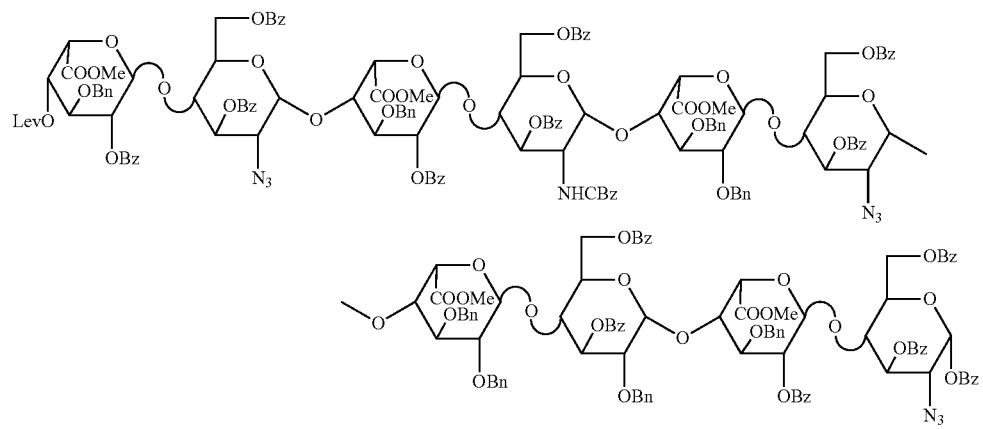

Structure (ii) provided below is a combination of the following disaccharides 2-3-4-1-2:

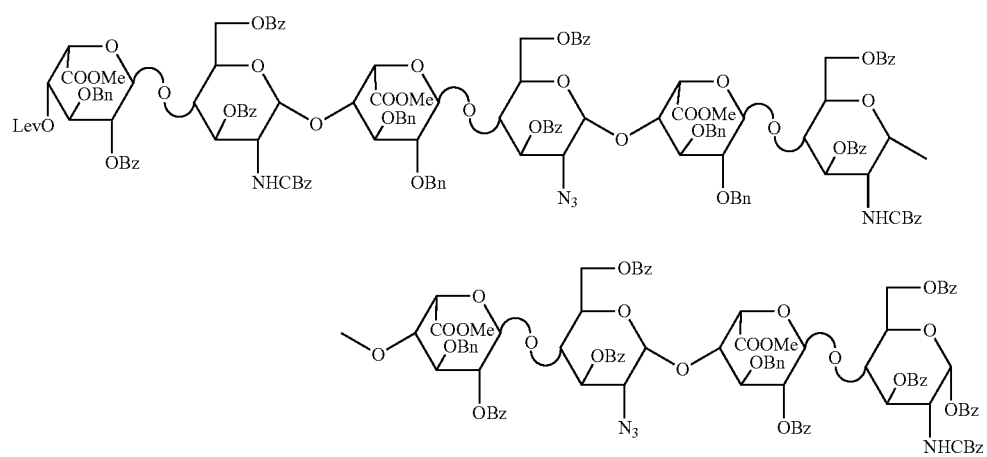

Structure (iii) provided below is a combination of the following disaccharides 1-3-2-4-3:

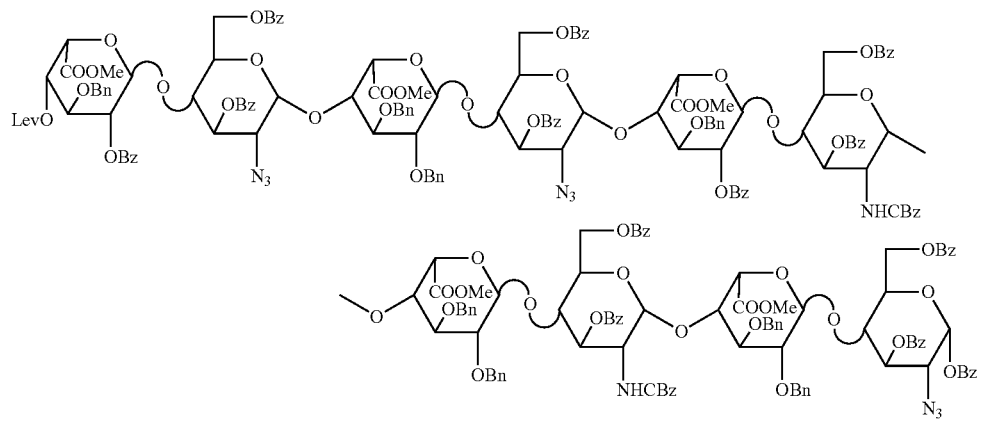

Such methods can be used to provide a collection or library of protected oligosaccharides, e.g., having any combination of disaccharides described herein, e.g., any combination of disaccharides 1-16 of Table I or of disaccharides 1-16 of Table II. The oligosaccharide can then be deprotected at a class of protected positions, e.g., positions having a protecting group that allows derivatization, e.g., sulfation, to provide an oligosaccharide with unprotected moieties and forming substituents, e.g., derivative moieties, e.g., sulfate moieties. An oligosaccharide having a class of deprotected moieties at various positions in the oligosaccharide can be, e.g., sulfated at those positions using known techniques. For example, the oligosaccharide can be treated with sulfur trioxide-pyridine complex (e.g., with pyridine as solvent) to sulfate the deprotected moieties. For example, protected decasaccharides of structures i, ii and iii, provided above, can be treated with sulfur-trioxide-pyridine complex in the presence of pyridine, to provide the following derivatized oligosaccharides. Example 7 depicts such a procedure being followed on a disaccharide as an experimental proof of concept.

Other exemplary methods of providing an oligosaccharide having a preselected sequence are described in FIGS. 8 to 11. Oligosaccharides described in these Figures are embodiments of the disclosure.

EXAMPLES

Example 1

Synthesis of Glucosamine Synthon

Figure 12:
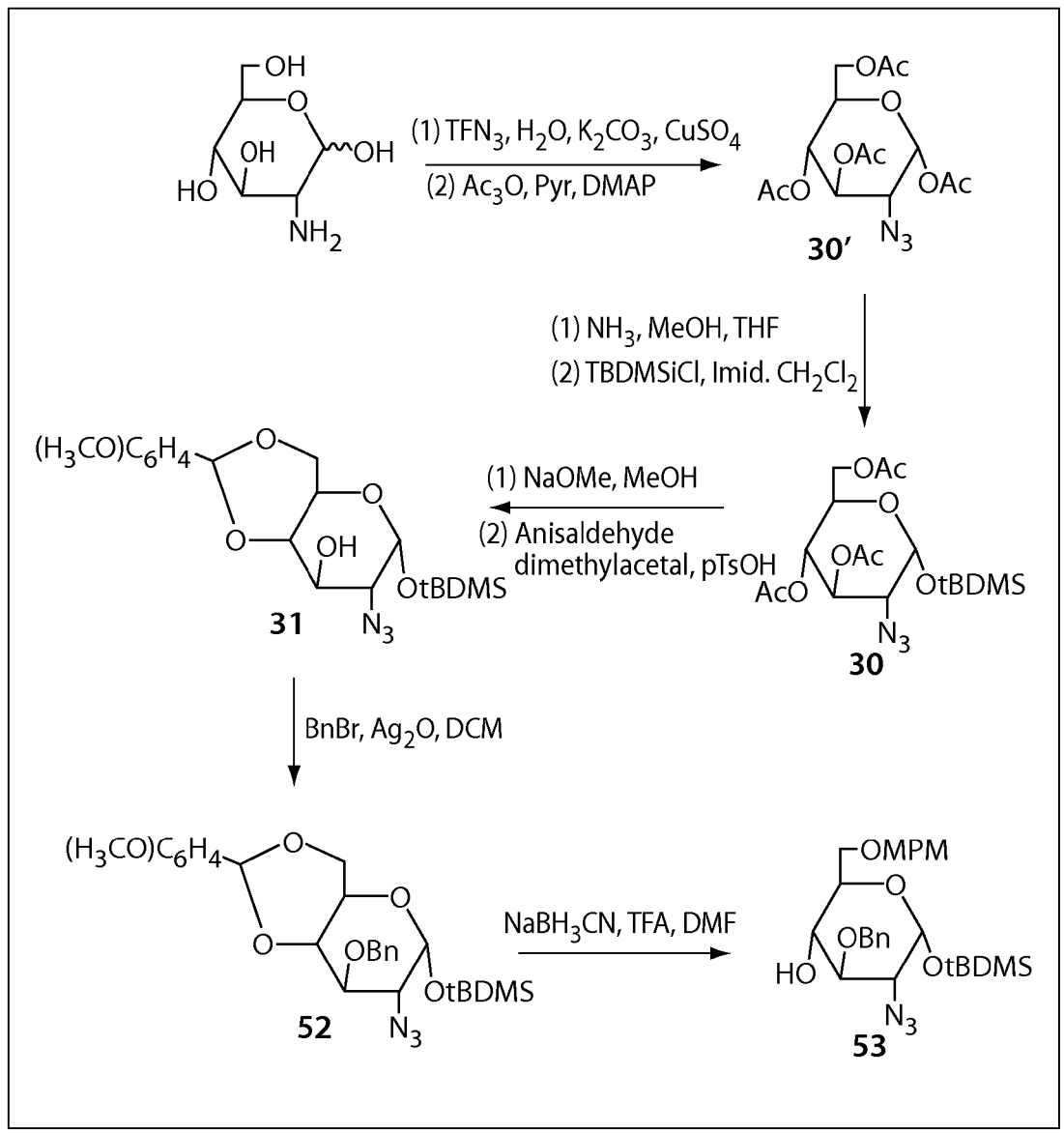
FIG. 12 depicts the synthesis of a diversely protected Glucosamine synthon.

The synthesis of the Glucosamine synthon is depicted in FIG. 12.
Synthesis of Compound 30 of FIG. 12

Compound 30 was obtained from Glucosamine hydrochloride as a white solid as described by Orgueira, H. A. et. al. Chem. Eur. J. 2003, 9 (1), 140-69. The product was characterized by $^1$H NMR.
Synthesis of Compound 31 of FIG. 12

Compound 30 (14 g, 0.0314 mol) was dissolved in methanol (175 ml) and sodium methoxide (25% in MeOH, 2.1 ml) was added and reaction stirred for 15 mins. After 15 mins, Dowex-50 acidic resin was added to the above until the reaction mixture pH reached 6. The Dowex resin was subsequently filtered off and the solvent was removed under vacuum to afford a brown colored reaction mass. The crude compound was purified by column chromatography to obtain a yellow viscous oil as product (10 g, 100% yield).

This yellow viscous oil (10 g, 0.0313 mol) was co-evaporated with toluene and finally dissolved in dry acetonitrile (110 ml). p-Toluene sulphonic acid monohydrate (0.18 g, 0.00094 mol) and anisaldehyde dimethyl acetal (11.42 g, 0.0627 mol) were added and the reaction mass allowed to stir overnight at room temperature. On completion, triethyl amine (1.35 ml) was added and the solvent was removed under vacuum. Purification was carried out by flash chromatography on silica gel using 5% ethyl acetate as an eluant to afford pale yellow viscous oil as a product (8.8 g, 65% yield). The product was characterized by $^1$H NMR.
Synthesis of Compound 52 of FIG. 12

Compound 31 (27 g, 0.0619 mol) was dissolved in DCM (240 ml), to which 4 A° molecular sieves (43 g) and benzyl bromide (53.45 g, 0.30 mol) were added and the reaction allowed to stir for 30 mins at room temperature. Silver (I) oxide (41.5 g, 0.179 mol) was added and the reaction was stirred for 18 hrs in the dark. The silver (I) oxide was then filtered off through celite bed and the filtrate concentrated under vacuum. Isolation of the product was done by column chromatography using 5% ethyl acetate as an eluant to get white solid (20 g, 61.5% yield). The product was characterized by $^1$H NMR.
Synthesis of Compound 53 of FIG. 12

A mixture of Compound 52 (20 g, 0.037 mol) and sodium cyanoborohydride (11.87 g, 0.189 mol) in anhydrous DMF (270 ml) containing 4A° molecular sieves (9.6 g) was cooled to 0° C. under vigorous stirring. A solution of trifluoroacetic acid (26 ml) in anhydrous DMF (146 ml) was added and reaction stirred for additional 2 h at 0° C. After 2 h the reaction mass was allowed to stir at room temperature for 18 h. On completion, reaction was quenched with triethylamine and then filtered and concentrated under vacuum. The residue was dissolved in dichloromethane and then washed with saturated sodium bicarbonate, dried over anhydrous sodium sulphate and concentrated in vacuum, before purification by preparative HPLC. Yield: 8 g (40%). The product was characterized by $^1$H NMR.

Example 2

Synthesis of Iduronic Acid Synthons

Figure 13:
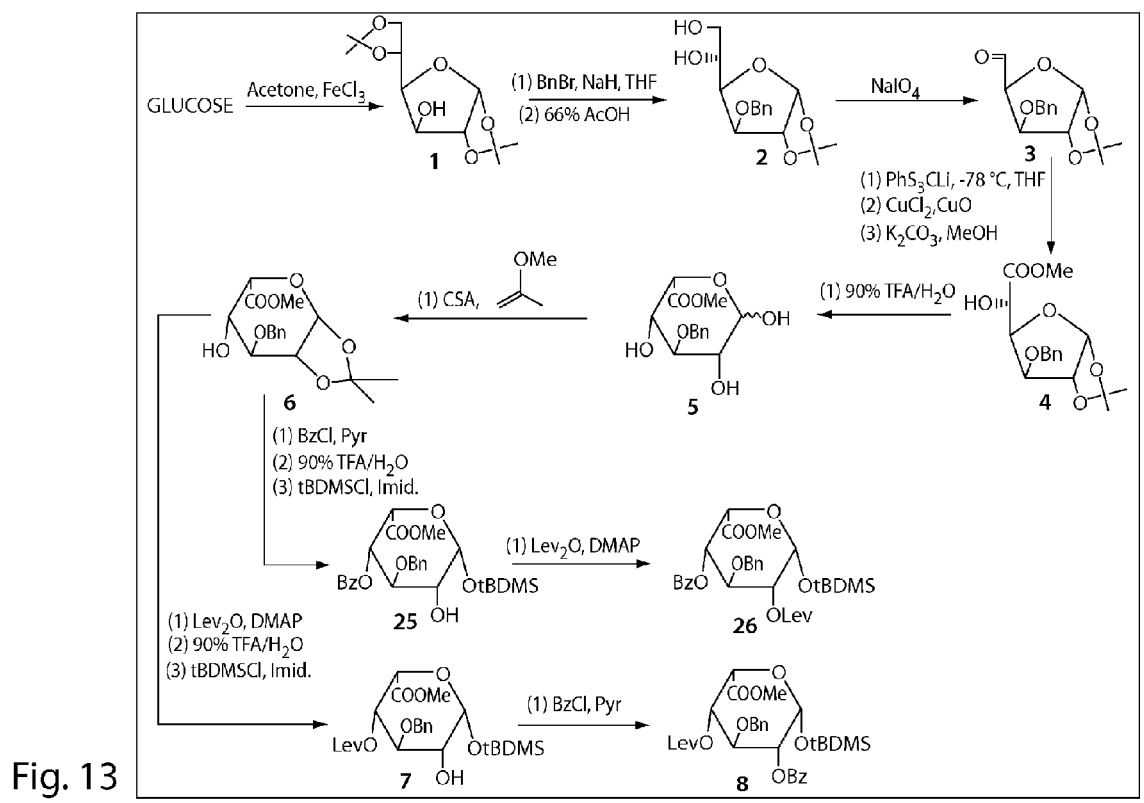
FIG. 13 depicts the synthesis of diversely protected Iduronic acid synthons.

The synthesis of the Iduronic acid synthons is depicted in FIG. 13.

Synthesis of Compound 6 of FIG. 13

Compound 6 was obtained from diacetone glucose (Compound I) through a series of chemical transformations as detailed in Lohman, G. J. S. et. al. J. Org. Chem. 2003, 68 (19), 7559-7561.

Synthesis of Compound 7 of FIG. 13

Compound 6 (14.0 g) was dissolved in DCM (100 ml) and cooled to 0° C. To this was added levulinic acid (7.7 g), DIPC (9.7 ml) and DMAP (8.1 g) at 0° C. and light was excluded. The reaction was stirred overnight at room temperature. On completion, the reaction mixture was diluted with EtOAc: Hexane (1:1, 200 ml), passed through a silica plug, concentrated and subjected to flash column chromatography using hexane: EtOAc system to yield yellow oil (12.5 g). The product was characterized by $^1$H NMR and LC/MS.

The yellow oil from previous step (12.5 g) was dissolved in trifluoroacetic acid (90% aqueous, 100 ml) and was stirred for 1 hr. The solvent was removed under vacuum and by co-evaporation with toluene. After removal of TFA, the reaction mixture was dissolved in DCM (50 ml), and Imidazole (3.9 gm) and tert-butyl dimethyl silyl chloride (4.75 g) were added. The reaction mixture was stirred overnight at room temperature. The reaction mixture was then diluted with ethyl acetate, washed with water, 1N HCl and water, dried, concentrated and subjected to flash column chromatography using Hexane: EtOAc solvent system to yield Compound 7 (9.1 g). The product was characterized by $^1$H NMR and LC/MS.

Synthesis of Compound 8 of FIG. 13

Compound 7 (5.0 g) was dissolved in DCM (10 ml) and cooled to 0° C. and to this was added pyridine (2.0 ml) at 0° C. under nitrogen. The resultant solution was stirred for 10 minutes and benzoyl chloride (1.5 ml) was added. The reaction mixture was then stirred for 48 hrs (at 7-8° C.) under nitrogen. The reaction mixture was then diluted with DCM (50 ml), washed with water, 1N.HCl, 10% sodium bicarbonate and brine solution. This was dried, concentrated and subjected to flash column chromatography using Hexane: EtOAc solvent system to yield pure Compound 8 (3.7 g). The product was characterized by $^1$H NMR and LC/MS.

Synthesis of Compound 25 of FIG. 13

Compound 6 (12.0 gm) was dissolved in DCM (35 ml) and cooled to 0° C. and to this was added pyridine (7.2 ml). The solution was then stirred for 10 minutes following which benzoyl chloride (5.5 ml) was added. This reaction mixture was then stirred for 48 hrs (at 7-8° C.) under nitrogen. On completion, the reaction mixture was diluted with DCM (50 ml), washed with water, 1N HCl, 10% sodium bicarbonate and brine solution. The organic layers was dried, concentrated and subjected to flash column chromatography using Hexane: EtOAc solvent system to yield compound (10.0 gm). The product was characterized by $^1$H NMR and LC/MS.

Compound from previous step (9.0 gm) was dissolved in trifluoroacetic acid (90% aqueous, 72 ml)) and stirred for 1 hour. The solvent was removed under vacuum by co-evaporation with toluene. The resultant oil was dissolved in DCM (50 ml), and imidazole (3.1 gm) and tert-butyl dimethyl silyl chloride (3.75 gm) added. The reaction mixture was stirred overnight at room temperature. On completion, the reaction mixture was diluted with ethyl acetate, washed with water, 1N HCl and water, dried, concentrated and subjected to flash column chromatography using Hexane: EtOAc solvent system to yield Compound 25 (6.0 gm). The product was characterized by $^1$H NMR and LC/MS.

Synthesis of Compound 26 of FIG. 13

Compound 25 (6.0 gm) was dissolved in DCM (100 ml) and cooled to 0° C. To this was added Levulinic acid (1.9 ml), DIPC (2.7 ml) and DMAP (2.3 gm) at 0° C. and reaction stirred overnight at room temperature under light exclusion. The reaction mixture was diluted with EtOAc:Hexane (1:1, 100 ml) and passed through a silica plug. It was then concentrated and subjected to column chromatography using Hexane:EtOAc system to yield pure Compound 26 (4.0 gm). The product was characterized by $^1$H NMR and LC/MS.

Example 3

Figure 14:
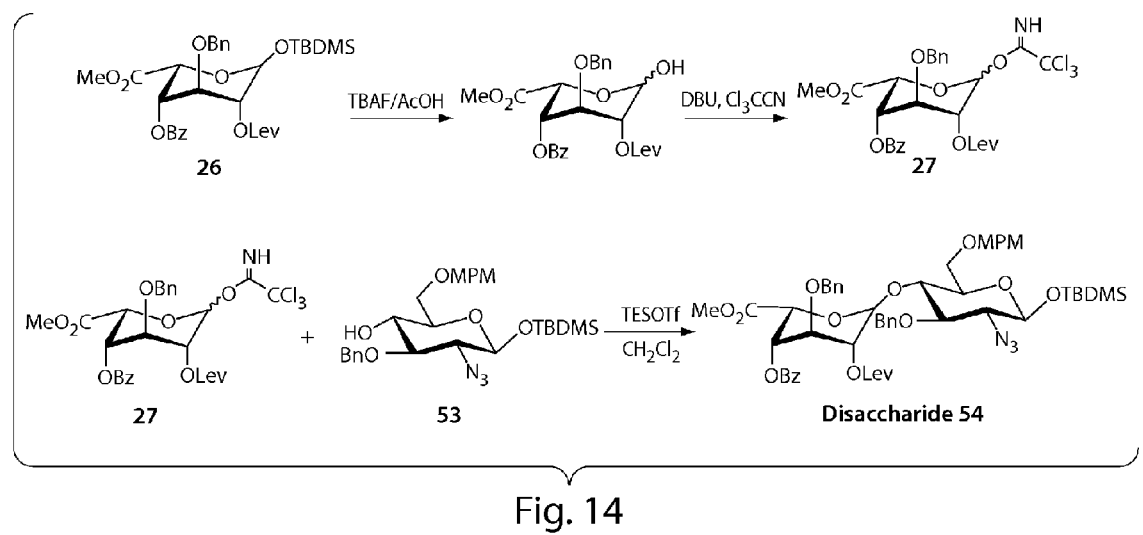
FIG. 14 depicts the synthesis of a diversely protected disaccharide.

Synthesis of Disaccharide 54 of FIG. 14

The synthesis of Disaccharide 54 is depicted in FIG. 14.

1. Generation of Disaccharide Donor 27 of FIG. 14

Compound 26 (0.62 g, 0.1 mmol) was dissolved in freshly distilled THF (10 mL) and cooled to 0° C. To this was added, glacial acetic acid (110 μL, 2.0 mmol) followed by TBAF (1.0M in THF, 2.0 mL). The reaction mixture was stirred for 30 min at 0° C. and then diluted with 200 mL of ethyl acetate. The organic layer was washed with NH$_4$Cl, NaHCO$_3$, brine, and then water, dried over anhydrous Na$_2$SO$_4$, filtered and concentrated to yield a yellow oil (461 mg) which was used without further purification in the next step.

The crude oil obtained was co-evaporated with toluene under high vacuum and dissolved in dry dichloromethane (10 mL). The solution was cooled to 0° C. and trichloroacetonitrile (1.0 mL, 10 mmol) and DBU (14 μL, 0.1 mmol) were added. The reaction mixture was stirred for 20 min at 0° C. and then poured onto a flash chromatography column on silica gel to obtain pure Compound 27 (415 mg, 63% yield). The compound was characterized by $^1$H NMR.

2. Synthesis of Disaccharide 54 of FIG. 14

The trichloroacetimidate (Compound 27, 415 mg, 0.64 mmol) and the Compound 53 (320 mg, 0.58 mmol) were combined and dissolved in dry dichloromethane (10 mL). 4 Å molecular sieves (0.5 g) was added and the mixture was stirred for 15 min at room temperature. Triethylsilyl trifluoromethanesulfonate (65 μL, 0.25 mmol) was added at room temperature. After 30 min, the reaction was quenched with triethylamine, concentrated under reduced pressure and the residue was purified by flash chromatography on silica gel to give a 'α and β' disaccharide mixture (408 mg, α:β=6:1). Further purification by column chromatography yielded pure α Disaccharide 54 (310 mg). The compound was characterized by $^1$H NMR, $^{13}$C NMR, 2D NMR(HSQC, COSY, TOCSY) and ESI-MS.

Example 4

Figure 15:
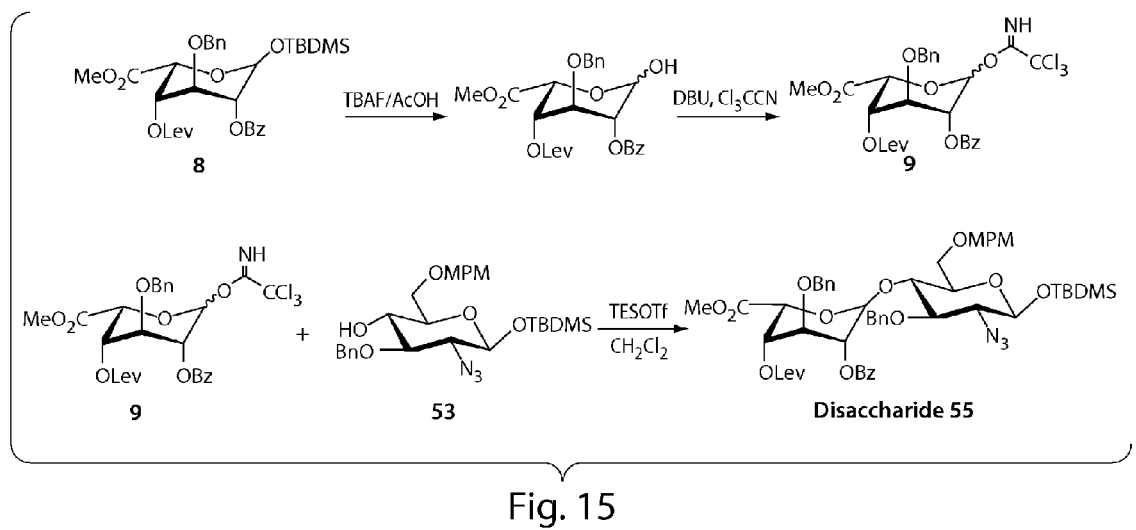
FIG. 15 depicts the synthesis of a diversely protected disaccharide.

Synthesis of Disaccharide 55 of FIG. 15

The synthesis of Disaccharide 55 is depicted in FIG. 15.

1. Synthesis of Disaccharide Donor 9 of FIG. 15

Compound 8 (1.2 g) was dissolved in freshly distilled THF (10 mL) and cooled to 0° C. To this was added glacial acetic acid (110 μL, 2.0 mmol) followed by THF (1.0 M of TBAF, 1.94 mL). The reaction mixture was stirred for 15 min and then diluted with 200 mL of ethyl acetate. The organic layer was washed with NH$_4$Cl, NaHCO$_3$, brine, and water and then dried over anhydrous Na$_2$SO$_4$, filtered and then concentrated to yield a light yellow oil (560 mg). This compound was used without further purification in the next step. Crude compound was dissolved in dry dichloromethane (8 mL). The solution was cooled to 0° C., and trichloroacetonitrile (1.0 mL, 10 mmol) and DBU (14 µL, 0.1 mmol) were added. The reaction mixture was stirred for 20 min and then poured onto flash chromatography column on silica gel to yield Compound 9 (320 mg, 51% yield). The compound was characterized by $^1$H NMR.

2. Synthesis of Disaccharide 55 of FIG. 15

Trichloroacetimidate 9 (320 mg, 0.5 mmol) and compound 53 (240 mg, 0.45 mmol) were combined and dissolved in anhydrous dichloromethane (10 mL). 4A Molecular sieves (0.5 g) and triethylsilyl trifluoromethanesulfonate (40 µL, 0.2 mmol) was added and the mixture was stirred for 15 min at room temperature. On completion, the reaction was quenched with triethylamine, concentrated under reduced pressure and the residue was purified by flash chromatography on silica gel to give an 'α and β' disaccharide mixture (300 mg total, α:β=5:1). Further purification by column chromatography afforded pure α form of Disaccharide 55 (210 mg). The compound was characterized by $^1$H NMR, $^{13}$C NMR, 2D NMR (HSQC, COSY, TOCSY) and ESI-MS.

Example 5

Synthesis of Tetrasaccharide 59 of FIG. 16

The synthesis of Tetrasaccharide 59 is depicted in FIG. 16.
1. Synthesis of Disaccharide Acceptor 56 of FIG. 15

Disaccharide 55 (0.41 g, 0.4 mmol) was dissolved in 5 mL of MeOH and 5 mL of 1% NaOH in MeOH was added at 0° C. and the reaction mixture subsequently warmed to room temperature. The reaction mixture was stirred for 1 hour and acetic acid (AcOH) was added to quench the reaction. The reaction mixture was concentrated and the residue was purified by flash column chromatography to yield 235 mg of acceptor 56 as a white solid (72% yield). The compound was characterized by $^1$H NMR.

2. Synthesis of Disaccharide Donor 57 of FIG. 15

Disaccharide 54 (710 mg, 0.7 mmol) was dissolved in freshly distilled THF (15 mL), solution cooled to 0° C. and acetic acid (92 µL, 1.5 mmol) was added, followed by TBAF (1.0 M in THF, 1.4 mL). The reaction mixture was kept stirring for 20 min and diluted with 100 mL of ethyl acetate. The organic layer was washed with NH$_4$Cl, NaHCO$_3$, brine, and water and then dried over anhydrous Na$_2$SO$_4$. The sample was filtered and concentrated to yield a yellow oil (610 mg).

The crude oil thus obtained, was dissolved in anhydrous dichloromethane (15 mL). The solution was then cooled to 0° C., and trichloroacetonitrile (0.7 mL, 7 mmol) and DBU (10 µL, 0.07 mmol) were added. The reaction mixture was stirred for 20 min and then poured onto a flash chromatography column on silica gel to purify disaccharide 57 (502 mg, 68% yield). The compound was characterized by $^1$H NMR.

3. Assembly of Tetrasaccharide 59 of FIG. 16

Trichloroacetimidate 57 (302 mg, 0.29 mmol) and disaccharide acceptor 56 (235 mg, 0.29 mmol) were combined and dissolved in anhydrous toluene (15 mL). 4° A molecular sieves (1 g) and triethylsilyl trifluoromethanesulfonate (26 µL, 0.12 mmol) was added at −60° C. The reaction mixture was stirred for one hour. The reaction was then quenched with triethylamine, filtered and concentrated under reduced pressure. The residue was purified by flash chromatography on silica gel to give α- and β-tetrasaccharides. Further purification (flash chromatography on silica gel) afforded the pure α form of tetrasaccharide 58 (65 mg, 13% yield). The compound was characterized by $^1$H NMR, $^{13}$C NMR, 2D NMR (HSQC, COSY, TOCSY) and ESI-MS.

Tetrasaccharide 58 (65 mg, 0.038 mmol) was dissolved in a mixture of 2 mL dry CH$_2$Cl$_2$ and 0.5 mL of anhydrous pyridine. To this was added, Lev$_2$O (39 mg, 0.19 mmol) and a small amount of DMAP at room temperature. After 30 min, the reaction mixture was diluted with 50 mL of CH$_2$Cl$_2$ and the organic layer was washed with cold NaHCO$_3$, 1% HCl, and water. After drying over anhydrous Na$_2$SO$_4$, the solution was filtered and concentrated. The remaining residue was purified by flash chromatography to yield the desired final tetrasaccharide 59 (60 mg, 88% yield). The compound was characterized by $^1$H NMR, $^{13}$C NMR, 2D NMR(HSQC, COSY, TOCSY) and ESI-MS.

Example 6

Synthesis of Hexasaccharide 62 of FIG. 17

The synthesis of Hexasaccharide 60 is depicted in FIG. 17.
1. Synthesis of Tetrasaccharide Acceptor 60 of FIG. 17

Tetrasaccharide 58 (0.18 g, 0.11 mmol) was dissolved in 5 mL of MeOH. 5 mL of 1% NaOH in MeOH was added at 0° C. and the reaction mixture was subsequently stirred at room temperature for another 4 hours after which time the reaction was quenched by addition of AcOH. The reaction mixture was concentrated and the residue was purified by flash column chromatography to give 68 mg of white solid (Tetrasaccharide 60, 43% yield). The compound was characterized by $^1$H NMR.

2. Assembly of Hexasaccharide 62 of FIG. 17

Trichloroacetimidate disaccharide 57, (48 mg, 0.046 mmol) and tetrasaccharide acceptor 60 (68 mg, 0.045 mmol) were combined and dissolved in dry toluene (8 mL). 4° A Molecule sieves (100 mg) and triethylsilyl trifluoromethanesulfonate (4.1 µL, 0.011 mmol) was added at −60° C. and the mixture was stirred for one hour. The reaction was then quenched with triethylamine, the mixture filtered and then concentrated under reduced pressure. The residue was purified by flash chromatography on silica gel to give a mixture of α and β hexasaccharides and further purification by flash chromatography afforded the pure α form hexasaccharide 61 (10 mg, 9% yield). The compound was characterized by $^1$H NMR, $^{13}$C NMR, 2D NMR(HSQC, COSY, TOCSY) and ESI-MS.

Hexasaccharide 61 (10 mg, 0.004 mmol) was dissolved in a mixture of 2 mL of dry CH$_2$Cl$_2$ and 0.5 mL of anhydrous pyridine. To this was added Lev$_2$O (4 mg, 0.02 mmol) and a small amount of DMAP at room temperature. After 30 min, the reaction mixture was diluted with 20 mL of CH$_2$Cl$_2$ and the organic layer was washed with cold NaHCO$_3$, 1% HCl and water. After drying over anhydrous Na$_2$SO$_4$, the mixture was filtered, concentrated and the residue was then purified by column chromatography to yield the desired final hexasaccharide, 62 (8 mg, 75% yield). The compound was characterized by $^1$H NMR, $^{13}$C NMR, 2D NMR(HSQC, COSY, TOCSY) and ESI-MS.

Example 7

Synthesis of Monosulfated Disaccharide 63

Figure 18:
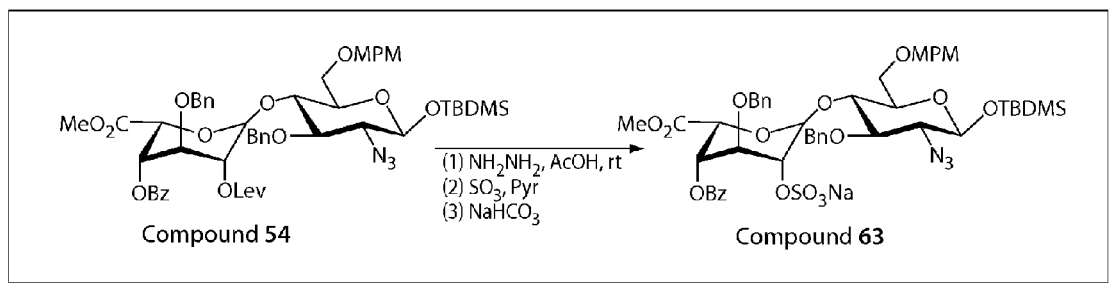
FIG. 18 depicts the synthesis of a monosulfated disaccharide.

The synthesis of the monosulfated Disaccharide 63 is shown in FIG. 18.

Disaccharide 54 (0.1 g, 0.099 mmol) was dissolved in 8 mL of EtOH/Toluene (2/1 v/v) and hydrazine acetate (91 mg, 0.99 mmol) was added at room temperature. The reaction mixture was stirred for 2 hours and then diluted with ethyl acetate (20 mL). The organic layer was washed with water, dried with NaSO₄, filtered, and concentrated via evaporation. The resulting residue was purified by column chromatography on silica gel to provide 88 mg (98% crude yield) of C-20H compound to be used in the next step.

Crude compound from previous step (44 mg, 0.048 mmol) was dissolved in 5 mL of pyridine and sulfur-trioxide pyridine complex (SO₃ Py, 23 mg, 0.144 mmol) was added. The reaction mixture was left to stir at 45° C. for 3 hours after which MeOH was added to quench the reaction. The mixture was then concentrated and the resulting residue was purified by column chromatography on silica gel to give the C-2 O-sulphated compound as a 'pyridine' salt. Dried pyridinium salt was dissolved in 5 mL of MeOH and then 1 mL of NaHCO₃ (10% aqueous) was added. The reaction mixture was then concentrated to give crude sodium salt product which was purified by flash chromatography to yield the final product as the 'sulfated sodium salt' (Compound 63, 45 mg, 94% yield).

What is claimed:

1. A method of making an oligosaccharide with a preselected pattern of sulfation and/or acetylation, the oligosaccharide comprising disaccharide units, wherein the identity of each disaccharide unit is independent of the identity of the other disaccharide units within the oligosaccharide, and wherein the oligosaccharide is a tetrasaccharide, a hexasaccharide, an octasaccharide, or a decasaccharide, the method comprising:

providing a protected oligosaccharide comprising disaccharide units, wherein the identity of each disaccharide unit is independent of the identity of the other disaccharide units within the protected oligosaccharide, wherein the protected oligosaccharide is a tetrasaccharide, a hexasaccharide, an octasaccharide, or a decasaccharide, and wherein the protected oligosaccharide comprises:

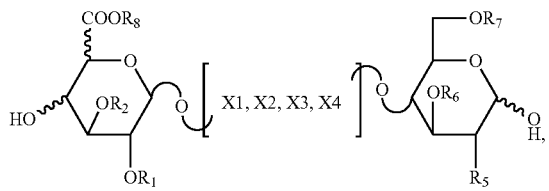

wherein each tetrasaccharide comprises X1, each hexasaccharide comprises X1 and X2, each octasaccharide comprises X1, X2, and X3, and each decasaccharide comprises X1, X2, X3, and X4 ; and wherein each of X1, X2, X3 and X4 is independently A or B, and wherein A is

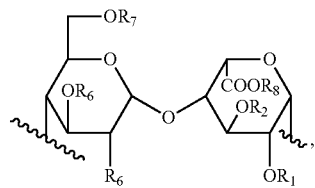

and
B is

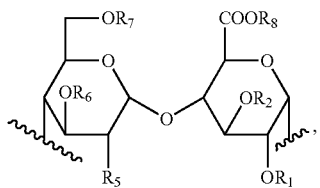

wherein $R_8$ for each occurrence of A or B is independently a hydrogen or an alkyl group, and wherein $R_5$ for each occurrence of A or B is an amine containing protecting group that, independently for each occurrence, is an amine containing protecting group selected from either a first amine containing protecting group that allows sulfation or acetylation or a second amine containing protecting group that does not allow sulfation or acetylation, and wherein $R_1$, $R_2$, $R_6$, and $R_7$ for each occurrence of A or B is a protecting group selected from either a first protecting group that allows sulfation or acetylation, or a second protecting group that does not allow sulfation or acetylation; and deprotecting the first protecting group to form an unprotected moiety or moieties and forming a sulfate or acetyl moiety at the deprotected position or positions, to thereby produce the oligosaccharide with the preselected pattern of sulfation and/or acetylation.

2. The method of claim 1, wherein the method further comprises purifying the oligosaccharide.

3. An oligosaccharide with a preselected pattern of sulfation and/or acetylation made by the method of claim 1.

4. A substantially pure preparation comprising an oligosaccharide with a preselected pattern of sulfation and/or acetylation made by the method of claim 1.

5. A pharmaceutical composition comprising an oligosaccharide with a preselected pattern of sulfation and/or acetylation made by the method of claim 1.

* * * * *